United States Patent
Hsiao et al.

(10) Patent No.: US 12,105,294 B2
(45) Date of Patent: *Oct. 1, 2024

(54) SYSTEMS AND METHODS FOR IMPROVING BINOCULAR VISION

(71) Applicant: HES IP HOLDINGS, LLC, Austin, TX (US)

(72) Inventors: Yung-Chin Hsiao, Taipei (TW); Yin Chang, Taipei (TW); Jiunn-Yiing Lai, New Taipei (TW)

(73) Assignee: HES IP HOLDINGS, LLC, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 18/450,032

(22) Filed: Aug. 15, 2023

(65) Prior Publication Data
US 2023/0384602 A1 Nov. 30, 2023

Related U.S. Application Data

(63) Continuation of application No. 17/637,808, filed as application No. PCT/US2021/049171 on Sep. 3, 2021, now Pat. No. 11,774,759.
(Continued)

(51) Int. Cl.
*G06F 3/01* (2006.01)
*G02B 27/01* (2006.01)
*G02B 27/00* (2006.01)

(52) U.S. Cl.
CPC ......... *G02B 27/0172* (2013.01); *G06F 3/013* (2013.01); *G02B 27/0093* (2013.01)

(58) Field of Classification Search
CPC .............. G02B 27/0172; G06F 3/013
See application file for complete search history.

(56) References Cited

U.S. PATENT DOCUMENTS

| 6,111,597 A | 8/2000 | Tabata |
| 10,616,568 B1 | 4/2020 | Lin et al. |

(Continued)

FOREIGN PATENT DOCUMENTS

| CN | 107438796 A | 12/2017 |
| CN | 108427498 A | 8/2018 |

(Continued)

OTHER PUBLICATIONS

International Search Report and Written Opinion mailed on Dec. 6, 2021, in a counterpart PCT application, No. PCT/US2021/049171.
(Continued)

*Primary Examiner* — Sanghyuk Park
(74) *Attorney, Agent, or Firm* — Chen Yoshimura LLP

(57) ABSTRACT

The present disclosure describes systems and methods for improving binocular vision, which generate a virtual image moving between two different depths to stimulate and then strengthen the weaker/abnormal eye of the viewer to eventually improve or even restore his/her binocular vision based on the viewer's eye information. The system comprises an eye tracking module and a virtual image module. The eye tracking module is configured to provide eye information of the viewer. The virtual image module configured to display a first virtual object by projecting multiple normal light signals to a viewer's first eye to form a normal image and corresponding multiple adjusted light signals to a viewer's second eye to form an adjusted image.

19 Claims, 19 Drawing Sheets

Related U.S. Application Data

(60) Provisional application No. 63/085,172, filed on Sep. 30, 2020, provisional application No. 63/085,161, filed on Sep. 30, 2020, provisional application No. 63/074,444, filed on Sep. 3, 2020.

(56) References Cited

U.S. PATENT DOCUMENTS

| | | |
|---|---|---|
| 11,079,601 B2 | 8/2021 | Greenberg |
| 11,256,092 B2 | 2/2022 | Shamir et al. |
| 2002/0024708 A1 | 2/2002 | Lewis et al. |
| 2002/0180868 A1 | 12/2002 | Lippert et al. |
| 2008/0117289 A1 | 5/2008 | Schowengerdt et al. |
| 2012/0002163 A1 | 1/2012 | Neal |
| 2015/0169070 A1 | 6/2015 | Harp et al. |
| 2015/0215608 A1 | 7/2015 | Tahara |
| 2016/0178908 A1 | 6/2016 | Dobschal et al. |
| 2016/0238845 A1 | 8/2016 | Alexander et al. |
| 2017/0068091 A1 | 3/2017 | Greenberg |
| 2017/0078651 A1 | 3/2017 | Russell |
| 2017/0295353 A1* | 10/2017 | Hwang ............... H04N 13/344 |
| 2018/0081322 A1 | 3/2018 | Robbins et al. |
| 2018/0120573 A1* | 5/2018 | Ninan ................. G02C 7/08 |
| 2018/0182174 A1* | 6/2018 | Choi ................. G02B 27/0075 |
| 2018/0252926 A1 | 9/2018 | Alexander et al. |
| 2018/0262758 A1 | 9/2018 | El-Ghoroury et al. |
| 2018/0284441 A1 | 10/2018 | Cobb |
| 2019/0064435 A1 | 2/2019 | Karafin et al. |
| 2019/0084419 A1 | 3/2019 | Suzuki et al. |
| 2019/0172216 A1* | 6/2019 | Ninan ................. H04N 13/128 |
| 2019/0187473 A1 | 6/2019 | Tomizawa et al. |
| 2019/0222830 A1 | 7/2019 | Edwin et al. |
| 2019/0285897 A1 | 9/2019 | Topliss et al. |
| 2019/0293939 A1 | 9/2019 | Sluka |
| 2019/0320165 A1 | 10/2019 | French et al. |
| 2019/0391638 A1 | 12/2019 | Khaderi et al. |
| 2020/0033603 A1* | 1/2020 | Ohkawa ............. G02B 27/0103 |
| 2020/0186787 A1 | 6/2020 | Cantero |
| 2020/0192475 A1 | 6/2020 | Gustafsson et al. |
| 2020/0241635 A1 | 7/2020 | Cohen |
| 2020/0249755 A1 | 8/2020 | Uscinski et al. |
| 2022/0311992 A1 | 9/2022 | Lai et al. |

FOREIGN PATENT DOCUMENTS

| | | |
|---|---|---|
| CN | 109073901 A | 12/2018 |
| CN | 109716244 A | 5/2019 |
| CN | 110168427 A | 8/2019 |
| JP | H4-501927 A | 4/1992 |
| JP | H08-166556 A | 6/1996 |
| JP | H09-105885 A | 4/1997 |
| JP | 2004-527793 A | 9/2004 |
| JP | 2007-121581 A | 5/2007 |
| JP | 2010-117542 A | 5/2010 |
| JP | 2011-13688 A | 1/2011 |
| JP | 2011-212430 A | 10/2011 |
| JP | 2016-180939 A | 10/2016 |
| JP | 2017-056933 A | 3/2017 |
| JP | 2018-508036 A | 3/2018 |
| JP | 2018-132756 A | 8/2018 |
| JP | 2018-533062 A | 11/2018 |
| KR | 20120069133 A | 6/2012 |
| TW | 201716827 A | 5/2017 |
| TW | 201809214 A | 3/2018 |
| WO | 91/04508 A2 | 4/1991 |
| WO | 2014/057557 A1 | 4/2014 |
| WO | 2016105281 A | 6/2016 |
| WO | 2021092314 A1 | 5/2021 |
| WO | 2022051688 A1 | 3/2022 |

OTHER PUBLICATIONS

Taiwanese Office Action, dated May 26, 2023, in a counterpart Taiwanese patent application, No. TW 110132945.
International Search Report and Written Opinion issued on Feb. 5, 2021, in a related PCT application, No. PCT/US2020/059317.
Taiwanese Office Action, issued on Aug. 23, 2022, in a related Taiwanese patent application, No. TW 109141615.
European Search Report, dated Nov. 21, 2023, in a counterpart or related EP patent application, No. EP 20886006.4.
Taiwanese Office Action, dated Nov. 27, 2023, in a counterpart or related Taiwanese patent application, No. TW 112112456.
European Search Report, dated Mar. 5, 2024, in a counterpart or related EP patent application, No. EP 21865240.2.
Japanese Office Action, dated Mar. 12, 2024, in a counterpart or related Japanese patent application, No. JP 2022-521209.

* cited by examiner

| Virtual binocular pixel | Pair of right pixel and left pixel | Address pointer |
|---|---|---|
| VBP(1) | RRI(1,1) & LRI(1,1) [R11 & L11] | Memory address 1 |
| VBP(2) | RRI(2,1) & LRI(1,1) [R21 & L11] | Memory address 2 |
| ... | ... | ... |
| VBP(7) | RRI(1,1) & LRI(2,1) [R11 & L21] | Memory address 7 |
| ... | ... | ... |
| VBP(37) | RRI(1,2) & LRI(1,2) [R12 & L12] | Memory address 37 |
| ... | ... | ... |
| VBP(216) | RRI(6,6) & LRI(6,6) [R66 & L66] | Memory address 216 |

FIG.15

SYSTEMS AND METHODS FOR IMPROVING BINOCULAR VISION

RELATED APPLICATION

This application claims the benefit of the provisional application 63/074,444, filed on Sep. 3, 2020, titled "SYSTEMS AND METHODS FOR BINOCULAR VISION CORRECTION," the provisional application 63/085,172, filed on Sep. 30, 2020, titled "SYSTEMS AND METHODS FOR PROJECTING VIRTUAL IMAGES WITH MULTIPLE DEPTHS," and the provisional application 63/085,161, filed on Sep. 30, 2020, titled "DYNAMIC IMAGE PROCESSING SYSTEMS AND METHODS FOR AUGMENTED REALITY DEVICES", which are incorporated herein by reference at their entireties.

In addition, the PCT international application PCT/US20/59317, filed on Nov. 6, 2020, titled "SYSTEM AND METHOD FOR DISPLAYING AN OBJECT WITH DEPTHS" is incorporated herein by reference at its entirety.

BACKGROUND OF THE INVENTION

Field of the Invention

The present disclosure relates generally to methods and systems for improving binocular vision and, in particular, to methods and systems for displaying a virtual object moving from a first position to a second position to improve the vision of a viewer's weak eye based on eye information of the viewer.

Description of Related Art

Amblyopia and strabismus are two of the most common eye disorders. Amblyopia is related to one of the eyes having significantly weaker vision over the other eye. It is oftentimes caused by abnormal visual development in early life of the patient. Amblyopia is the most common cause of decreased vision in a single eye among children and younger adults. Strabismus is related to the misalignment among two eyes of the patient. For patients have strabismus, one of the eyes may be turned in a different direction relative to the other eye. Most strabismus is caused by an abnormality of the neuromuscular control of the eye movement. Numerous methods for diagnosis and treatment have been proposed for amblyopia and strabismus. For amblyopia, the eye having weaker vision is usually corrected with glasses or contact lenses, or patching therapy; in some other cases, stimulation using frequency-contrast or color-contrast objects may improve the vision of the amblyopic eye. It has been proven that a combination of several types of stimulation is more effective. For strabismus, eye exercise is often used to improve the eye muscle correlation, so as to correct the misalignment among the two eyes. In recent years, there has been some progress in the use of medical devices to treat amblyopia and strabismus. However, these conventional devices cannot provide means for training binocular fixation between different depths. An innovative system and method for improving binocular vision is needed.

SUMMARY

The present disclosure relates to systems and methods for improving binocular vision of a viewer who has one eye abnormal or weaker than the other, by generating visual stimulus such as a virtual image to stimulate optic nerves in human eyes and to increase eye movements which may remedy eye conditions such as strabismus, amblyopia, convergence disorders, and other eye movement disorders. The normal eye is referred to as a first eye which may be the right eye or the left eye of the viewer. The weaker or abnormal eye (collectively the "weak eye") is referred to as a second eye which may be the right eye or the left eye of the viewer (the remaining eye other than the normal eye). The present disclosure describes systems and methods that generate a virtual image moving between two different depths to stimulate and then strengthen/remedy the weak eye of the viewer to eventually improve or even restore his/her binocular vision based on the viewer's eye information.

A system for improving binocular vision comprises an eye tracking module and a virtual image module. The eye tracking module is configured to track the viewer's both eyes and provide the related eye information, such as, pupil location, pupil size, gaze angle (view angle), and vergence angle of the viewer's each eye. Such eye information may be used to determine the whereabouts of the viewer's pupils and the viewer's fixation locations and fixation depths.

The virtual image module is configured to display a first virtual object by projecting multiple normal light signals to a viewer's first eye to form a normal image and corresponding multiple adjusted light signals to a viewer's second eye to form an adjusted image, based on eye information of the viewer, such as the locations of the viewer's both pupils. The first virtual object is displayed at a first targeted location and a first targeted depth. The viewer's first eye perceives the normal image of the first virtual object and the viewer's second eye perceives the adjusted image of the first virtual object. The first targeted depth is related to the first angel between the first normal light signal and the corresponding first adjusted light signal projected into the viewer's eyes.

Moreover, for the viewer's first eye to perceive the normal image and the viewer's second eye to perceive the adjusted image concurrently, the virtual image module may need to adjust the directions and locations the multiple normal light signals and the corresponding multiple adjusted lights signals to cause them respectively projected into the first eye and the second eye of the viewer based on the location of the viewer's pupils provided by the eye tracking module.

The virtual image module displays the first virtual object moving from the first targeted location and the first targeted depth to the second targeted location and the second targeted depth. The first targeted depth is different from the second targeted depth. The second targeted depth is related to a second angle between the second normal light signal and the corresponding second adjusted light signal. When the first virtual object moves, the viewer's eyes follow its movement. As a result, the moving of the first virtual object between two visual depth planes increases the movements of the weak eye, and provides more stimulation to the weak eye. As a result, the vision of the weak eye is improved and then binocular vision may eventually be reestablished.

The adjusted light signals projected to the viewer's second eye may change more in light direction than the normal light signals projected to the viewer's first eye, when the virtual image module displays the first virtual object moving from the first targeted location and the first targeted depth to the second targeted location and the second targeted depth. As a result, the weak eye has to move (exercise) more than the normal eye to follow the movement of the first virtual object. Alternatively, the normal light signals projected to the viewer's first eye do not change the light direction, when the virtual image module displays the first virtual object moving from a first targeted location and a first targeted depth to a second targeted location and a second targeted depth. In this situation, the first eye of the viewer does not need to move at all while the second eye of the viewer has to move more to follow the movement of the first virtual object.

To improve the vision of the viewer's weak eye, the virtual image module may differentiate the contrast and the spatial frequency of the normal image for the viewer's first eye from those of the adjusted image for the viewer's second eye. Specifically, the virtual image module is configured to generate the adjusted image having higher contrast or lower spatial frequency than the corresponding normal image.

The virtual image module may display the first virtual object, including selecting an appropriate contrast and spatial frequency, and the direction and speed of movement of the first virtual object, based on the visual evoked potential (VEP) of either or both the viewer's eyes. The system for improving binocular vision may further include a VEP measuring module to measure a VEP of the viewer's eyes.

When the viewer is able to practice fixation, the virtual image module may display the first virtual object at the viewer's fixation location and fixation depth provided by the eye tracking module. When the viewer moves his/her fixation from a first fixation location and a first fixation depth to a second fixation location and a second fixation depth, the virtual image module moves the first virtual object according to the viewer's fixation. The virtual image module may display a second virtual object at a predetermined location and a predetermined depth. When the viewer moves his/her fixation to cause the first virtual object to move within a predetermined spatial range of the second virtual object for a predetermined period of time, the second virtual object is altered to interact with or respond to the first virtual object.

Additional features and advantages of the disclosure will be set forth in the descriptions that follow, and in part will be apparent from the descriptions, or may be learned by practice of the disclosure. The objectives and other advantages of the disclosure will be realized and attained by the structure and method particularly pointed out in the written description and claims thereof as well as the appended drawings. It is to be understood that both the foregoing general description and the following detailed description are exemplary and explanatory and are intended to provide further explanation of the invention as claimed.

BRIEF DESCRIPTION OF THE DRAWINGS

FIG. 15 is a table illustrating an embodiment of a look up table in accordance with the present invention.

DETAILED DESCRIPTION OF PREFERRED EMBODIMENTS

The terminology used in the description presented below is intended to be interpreted in its broadest reasonable manner, even though it is used in conjunction with a detailed description of certain specific embodiments of the technology. Certain terms may even be emphasized below; however, any terminology intended to be interpreted in any restricted manner will be specifically defined as such in this Detailed Description section.

The present disclosure relates to systems and methods for improving binocular vision of a viewer who has one eye abnormal or weaker than the other. Some persons are born, by illness, or by accident, to have one eye abnormal or weaker than the other, such as the symptoms of strabismus (including exotropia, hypotropia, hypertropia, esotropia), amblyopia (lazy eye), convergence disorders, and other eye movement disorders. The normal eye is referred to as a first eye 50 which may be right eye or the left eye of the viewer. The weaker or abnormal eye (collectively the "weak eye") is referred to as a second eye 60 which may be the right eye or the left eye of the viewer (the remaining eye other than the normal eye). The present disclosure describes systems and methods that generate a virtual image moving between two different depths to stimulate and then strengthen/remedy the weak eye of the viewer to eventually improve or even restore his/her binocular vision based on the viewer's eye information.

Figure 1:
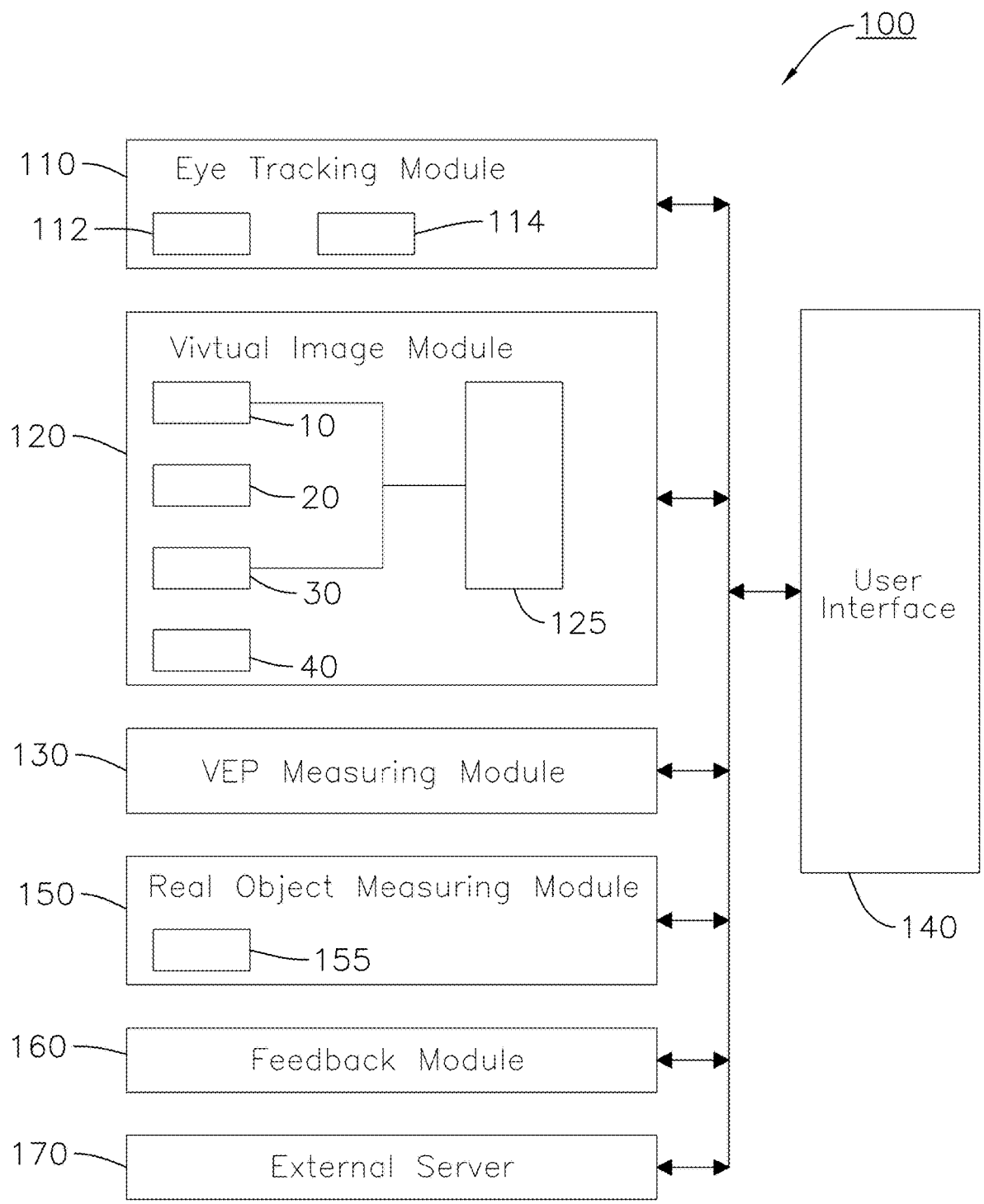
FIG. 1 is a block diagram illustrating an embodiment of a system with various modules in accordance with the present invention.

As shown in FIG. 1, a system for improving binocular vision comprises an eye tracking module 110 and a virtual image module 120. The eye tracking module 110 is configured to track a viewer's eyes and provide related eye information, such as eye movement, pupil location, pupil size, gaze angle (view angle), and vergence angle of the viewer's each eye. The eye tracking module may comprise a first camera 112 to track the first eye and a second camera 114 to track the second eye. The virtual image module 120 is configured to display a first virtual object, by projecting multiple normal light signals to a viewer's first eye to form a normal image and corresponding multiple adjusted light signals to a viewer's second eye to form an adjusted image, based on the viewer's eye information, such as locations of the viewer's both pupils. The virtual image module 120 includes a normal light signal generator 10, a normal combiner 20, an adjusted light signal generator 30, and an adjusted combiner 40. The normal light signal generator 10 generates multiple normal light signals which are redirected by a normal combiner to project into the viewer's first eye to form a normal image. The adjusted light signal generator 30 generates multiple adjusted light signals which are redirected by an adjusted combiner 40 to project into the viewer's second eye to form an adjusted image. The virtual image module 120 may further include a control unit 125 which can process and store data.

The system 100 may further comprise a VEP measuring module 130, a user interface 140, a real object measuring module 150, and a feedback module 160. The VEP measuring module 130 measures VEPs of the viewer's eyes, which are the electrical signals generated at the visual cortex in response to visual stimulation. The virtual image module 120 may display the first virtual object in a manner, based on the VEP of either or both the viewer's eyes. A user interface 140 allows the viewer or a trainer to control various functions of the system 100. The user interface 140 may be operated by voices, hand gestures, finger/foot movements and in the form of a pedal, a keyboard, a mouse, a knob, a switch, a stylus, a button, a stick, a touch screen, etc. The real object measuring module 150 measures a location and a depth of a real object, which interacts with the first virtual object. The real object measuring module 150 may also capture images and videos of the environment. The feedback module 160 provides feedbacks, such as sounds and vibrations, to the viewer if a predetermined condition is satisfied. An external server 170 is not part of the system 100 but can provide extra computation power for more complicated calculations. Each of these modules and the external server may communicate with each other via wired or wireless manner. The wireless manner may include WiFi, bluetooth, near field communication (NFC), internet, telecommunication, radio frequency (RF), etc.

Figure 2:
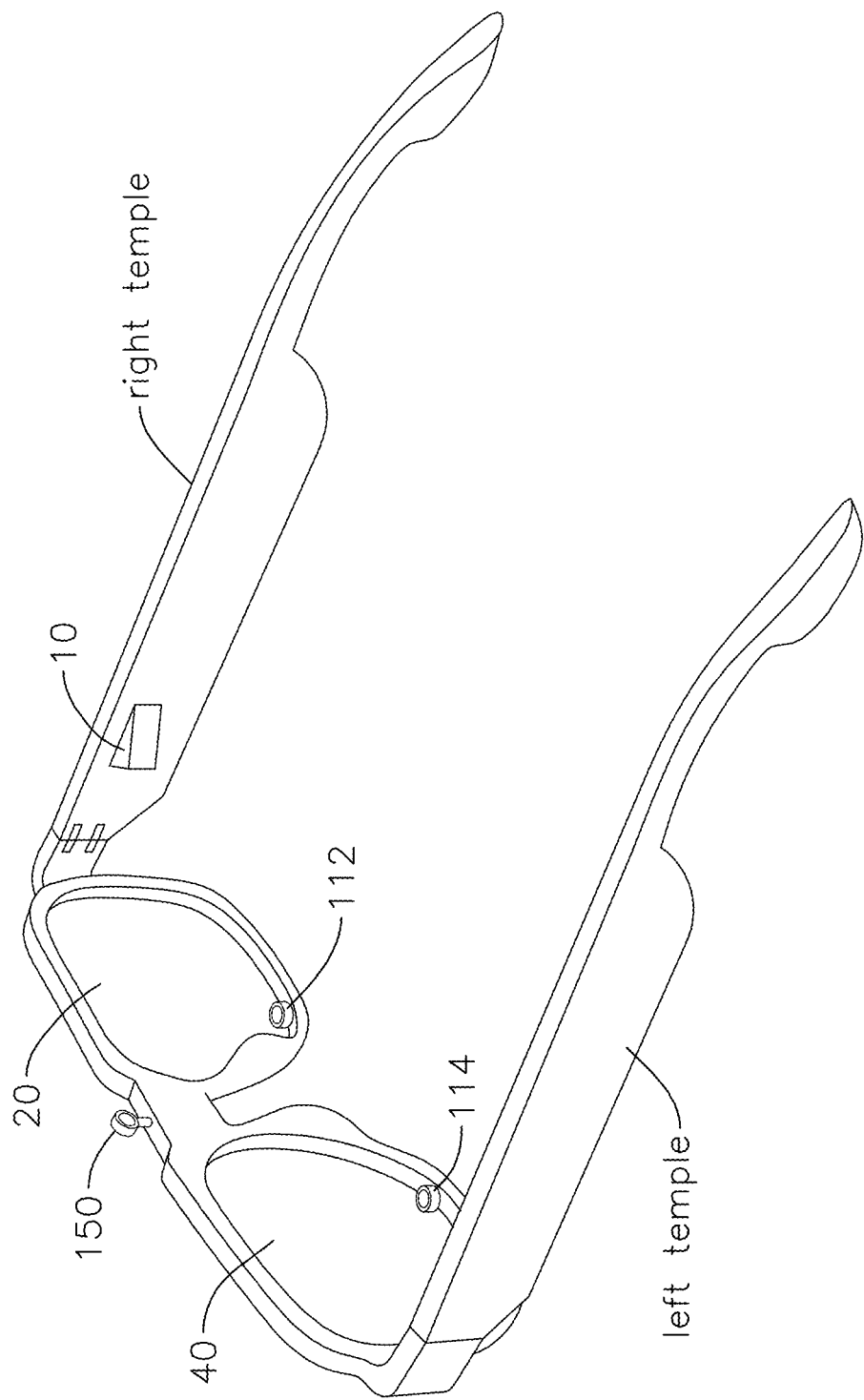
FIG. 2 is a schematic diagram illustrating an embodiment of a system for improving binocular vision as a head wearable device in accordance with the present invention.

As shown in FIG. 2, the system 100 further includes a support structure that is wearable on a head of the viewer. The normal light signal generator 10, the adjusted light signal generator the normal combiner 20, and the adjusted combiner 40 are carried by the support structure. In one embodiment, the system is a head wearable device, such as a virtual reality (VR) goggle and a pair of augmented reality (AR)/mixed reality (MR) glasses. In this circumstance, the support structure may be a frame with or without lenses of the pair of glasses. The lenses may be prescription lenses used to correct nearsightedness, farsightedness, etc. In addition, the eye tracking module, including the first camera 112 and the second camera 114, are carried by the support structure to track the viewer's both eyes. The real object measuring module 150 may be also carried by the support structure to measure the location and depth of a real object.

The eye tracking module 110 is configured to at least track locations of a viewer's both pupils. In addition, the eye tracking module may be configured to provide more information about the viewer's eyes, including but not limited to, eye movement, pupil size, gaze angle (view angle), and vergence angle of the viewer's each eye. Such eye information may be used to determine not only the directions and locations to project light signals for virtual objects but also the viewer's fixation locations and fixation depths. Again, the eye tracking module may comprise a first camera 112 to track the first eye 50 and a second camera 114 to track the second eye 60.

In addition to traditional eye tracking cameras, the first camera 112 and the second camera 114 may be built by the technologies of ultra-compact micro-electromechanical systems (MEMS). The first camera 112 and the second camera 114 may use ultra-red emitters and sensors to detect and derive various eye information. The eye tracking module 110 may further include an integrated inertial measurement unit (IMU), an electronic device that measures and reports a body's specific force, angular rate, and sometimes the orientation of the body, using a combination of accelerometers, gyroscopes, and sometimes magnetometers.

Figure 3:
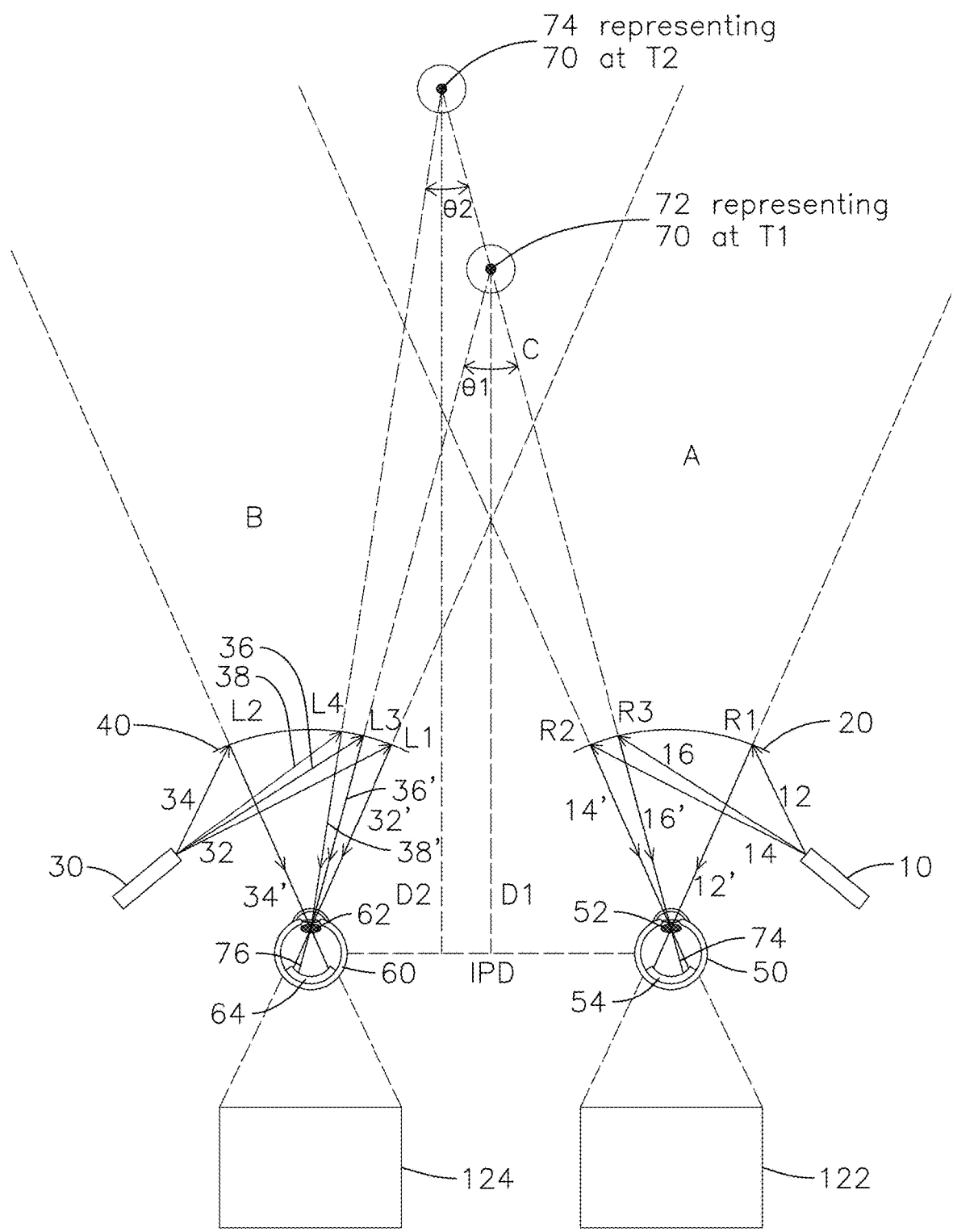
FIG. 3 is a schematic diagram illustrating an embodiment of a virtual image module in accordance with the present invention.

As shown in FIG. 3, the virtual image module 120 is configured to display a first virtual object 70, such as a tennis ball, by projecting multiple normal light signals to a viewer's first eye 50 to form a normal image 122 and corresponding multiple adjusted light signals to a viewer's second eye 60 to form an adjusted image 124, based on the viewer's eye information, such as the locations of both pupils 52, 62. The first virtual object 70 is displayed at a first targeted location and a first targeted depth (collectively the "first targeted position" or "T1"). The virtual image module 120 includes a normal light signal generator 10 to generate multiple normal light signals such as 12 for NLS_1, 14 for NLS_1 and 16 for NLS_3, a normal combiner 20 to redirect the multiple normal light signals towards the normal retina 54 of a viewer, an adjusted light signal generator 30 to generate multiple adjusted light signals such as 32 for ALS_1, 34 for ALS_2, and 36 for ALS_3, and an adjusted combiner 40 to redirect the multiple adjusted light signals towards an adjusted retina 64 of the viewer. The viewer has a normal eye 50 containing a normal pupil 52 and a normal retina 54, and a weak eye 60 containing an adjusted pupil 62 and an adjusted retina 64. The diameter of a human's pupil generally may range from 2 to 8 mm in part depending on the environmental lights. The normal pupil size in adults varies from 2 to 4 mm in diameter in bright light and from 4 to 8 mm in dark. The multiple normal light signals are redirected by the normal combiner 20, pass the normal pupil 52, and are eventually received by the normal retina 54. The normal light signal NLS_1 is the light signal farthest to the right the viewer's normal eye can see on a specific horizontal plan. The normal light signal NLS_2 is the light signal farthest to the left the viewer's normal eye can see on the same horizontal plane. Upon receipt of the redirected normal light signals, the viewer would perceive multiple normal pixels (forming the normal image) for the first virtual object 70 at the first targeted position T1 in the area A bounded by the extensions of the redirected normal light signals NLS_1 and NLS_2. The area A is referred to as the field of view (FOV) for the normal eye 50. Likewise, the multiple adjusted light signals are redirected by the adjusted combiner 40, pass the center of the adjusted pupil 62, and are eventually received by the adjusted retina 64. The adjusted light signal ALS_1 is the light signal farthest to the right the viewer's weak eye can see on the specific horizontal plan. The adjusted light signal ALS_2 is the light signal farthest to the left the viewer's weak eye can see on the same horizontal plane. Upon receipt of the redirected adjusted light signals, the viewer would perceive multiple adjusted pixels (forming adjusted image) for the first virtual object 70 in the area B bounded by the extensions of the redirected adjusted light signals ALS_1 and ALS_2. The area B is referred to as the field of view (FOV) for the weak eye 60. When both multiple normal pixels and adjusted pixels are displayed in the area C which are overlapped by area A and area B, at least one normal light signal displaying one normal pixel and a corresponding adjusted light signal displaying one adjusted pixel are fused to display a virtual binocular pixel with a specific depth in the area C. The first targeted depth D1 is related to an angle θ1 of the redirected normal light signal 16' and the redirected adjusted light signal 36' projected into the viewer's retinas. Such angle is also referred to as a convergence angle.

As described above, the viewer's first eye 50 perceives the normal image 122 of the first virtual object 70 and the viewer's second eye 60 perceives the adjusted image 124 of the first virtual object 70. For a viewer with appropriate image fusion function, he/she would perceive a single first virtual object at the first targeted location and the first targeted depth because his/her brain would fuse the normal image 122 and the adjusted image 124 into one binocular virtual image. However, if a viewer has a weak eye, he/she may not have appropriate image fusion function. In this situation, the viewer's first eye 50 and the second eye 60 may respectively perceive the normal image 122 at a first normal image location and depth, and the adjusted image 124 at a first adjusted image location and depth (double vision). The first normal image location and depth may be close to but different from the first adjusted image location and depth. In addition, the locations and depths of both the first normal image and first adjusted image may be close to the first targeted location and first targeted depth. Again, the first targeted depth D1 is related to the first angel θ1 between the first normal light signal 16' and the corresponding first adjusted light signal 36' projected into the viewer's eyes.

Moreover, for the viewer's first eye 50 to perceive the normal image 122 and the viewer's second eye 60 to perceive the adjusted image 124, the virtual image module 120 may need to adjust the directions and locations the multiple normal light signals and the corresponding multiple adjusted lights signals respectively projected into the first eye 50 and the second eye 60 of the viewer based on the location of the viewer's pupils provided by the eye tracking module 110.

The virtual image module 120 displays the first virtual object 70 moving from the first targeted position T1 to the second targeted location and the second targeted depth (collectively the "second targeted position" or "T2"). The first targeted depth D1 is different from the second targeted depth D2. The second targeted depth D2 is related to a second angle θ2 between the second normal light signal 16' and the corresponding second adjusted light signal 38'. The information from the eye tracking module, including the location and tracking capability of the viewer's both pupils, in particular those of the weak eye, are the factors to be considered for selecting the second targeted location and the second depth. The tracking capability of the viewer's eye can be assessed by whether and how soon the pupils follow the movement of the first virtual object. The better the tracking capability of the viewer's eyes is, the farther the second targeted position away from the first targeted position may be. When the virtual image module 120 displays the first virtual object 70 at the second targeted position T2 within the time period of persistence of vision, for example ⅛ second, after it displays the first virtual object at the first targeted position T1, the viewer's eyes perceive the first virtual object 70 moving from a first targeted position T1 to a second targeted position T2 and follow the movement. As a result, the moving of the first virtual object 70 between two visual depth planes increases the movements of the weak eye, including smooth pursuit and vergence eye movements, and provides more stimulation to the weak eye. As a result, the vision of the weak eye is improved and then binocular vision, including image fusion function, may eventually be reestablished.

Figure 4:
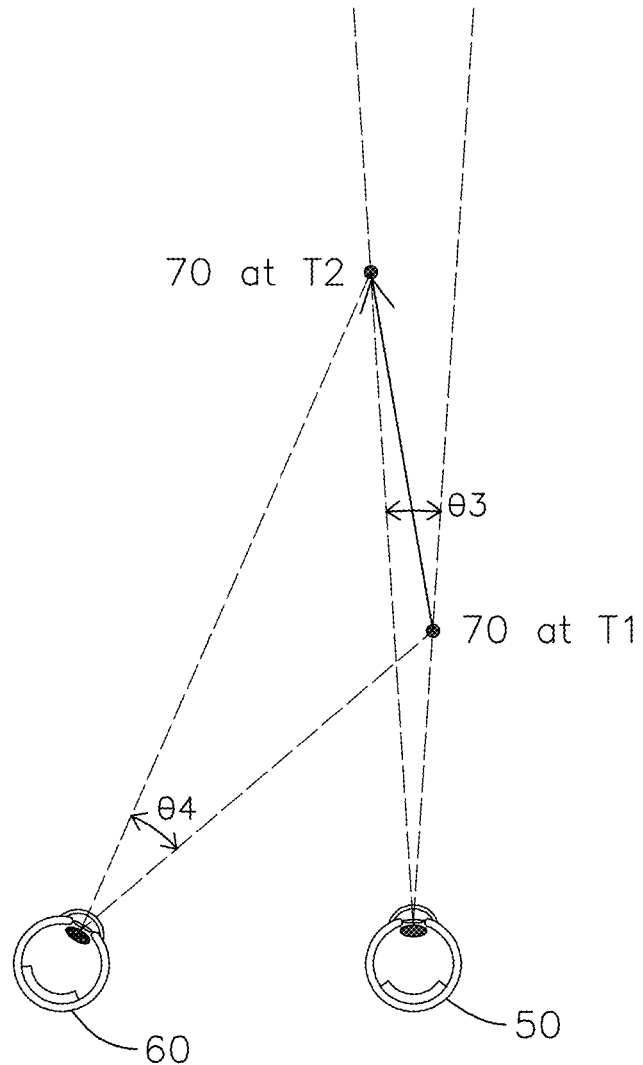
FIG. 4 is a schematic diagram illustrating an embodiment of moving a virtual object between two different depths in accordance with the present invention.
Figure 5A:
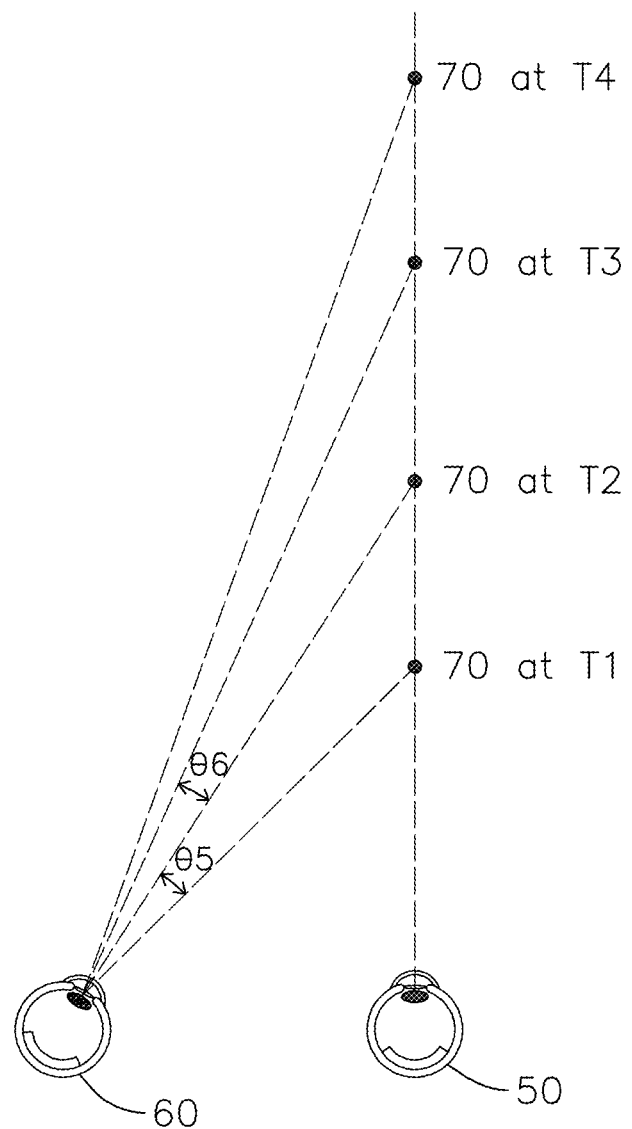
FIGS. 5A to 5C are schematic diagrams illustrating some embodiments of moving a virtual object between multiple different depths in accordance with the present invention.
Figure 5B:
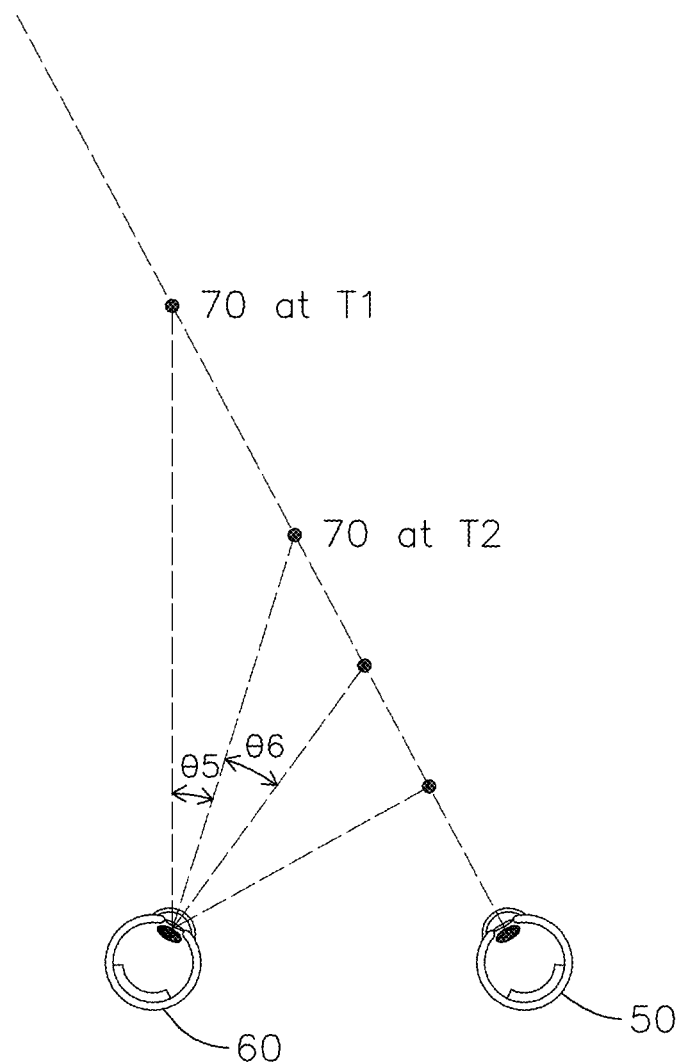
Figure 5C:
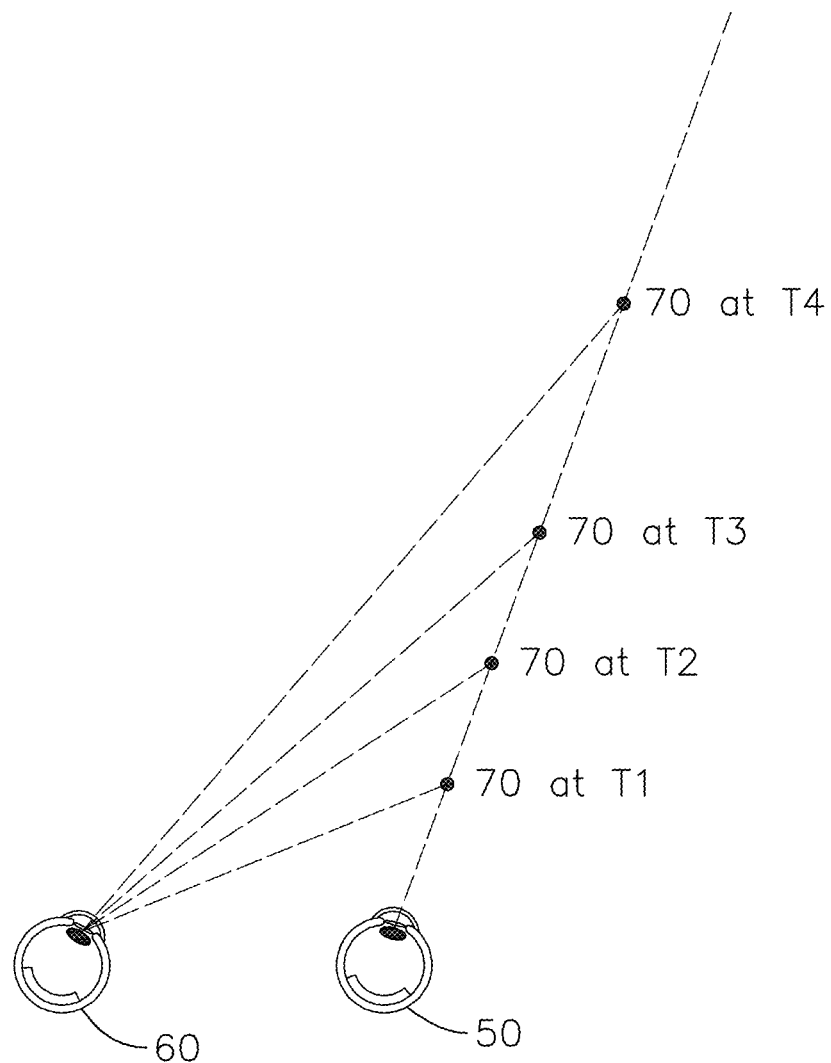

In one embodiment as shown in FIG. 4, the adjusted light signals projected to the viewer's second eye 60 change more in light direction than the normal light signals projected to the viewer's first eye 50, when the virtual image module 120 displays the first virtual object 70 moving from the first targeted position T1 to the second targeted position T2. In other words, θ4 is larger than θ3. As a result, the weak eye has to move (exercise) more than the normal eye to follow the movement of the first virtual object 70. In the strabismus and amblyopia condition, the more the weak eye exercises than the normal eye, the faster the gap of the vision between two eyes may be narrowed or even closed. In another embodiment as shown in FIGS. 5A-5C, the normal light signals projected to the viewer's first eye 50 do not change the light direction, when the virtual image module 120 displays the first virtual object 70 moving from a first targeted position T1 to a second targeted position T2. In this situation, the first eye 50 of the viewer does not need to move at all while the second eye of the viewer has to move more to follow the movement of the first virtual object. Based on the above described reason, the strabismus condition may be remedied more efficiently because the weak eye is forced to do all the movements.

After the first virtual object 70 is moved from the first targeted position T1 to the second targeted position T2, the virtual image module 120 may further display the first virtual object 70 moving from the second targeted position to a third targeted location and a third targeted depth (collectively the "third targeted position" or "T3"). Again, for the movement from the second targeted position T2 to the third targeted position T3, two alternative embodiments are (1) the adjusted light signals projected to the viewer's second eye 60 may change more in light direction than the normal light signals projected to the viewer's first eye 50 and (2) the normal light signals projected to the viewer's first eye 50 do not change the light direction as shown in FIGS. 5A-5C. Similarly, the virtual image module 120 may display the first virtual object 70 moving continuously through several targeted positions, such as T1→T2→T3→T4, depending on the needs of a training program.

Figure 6A:
FIGS. 6A and 6B are schematic diagrams illustrating an embodiment of the weak eye movement following the movement of a virtual object in accordance with the present invention.
Figure 6B:
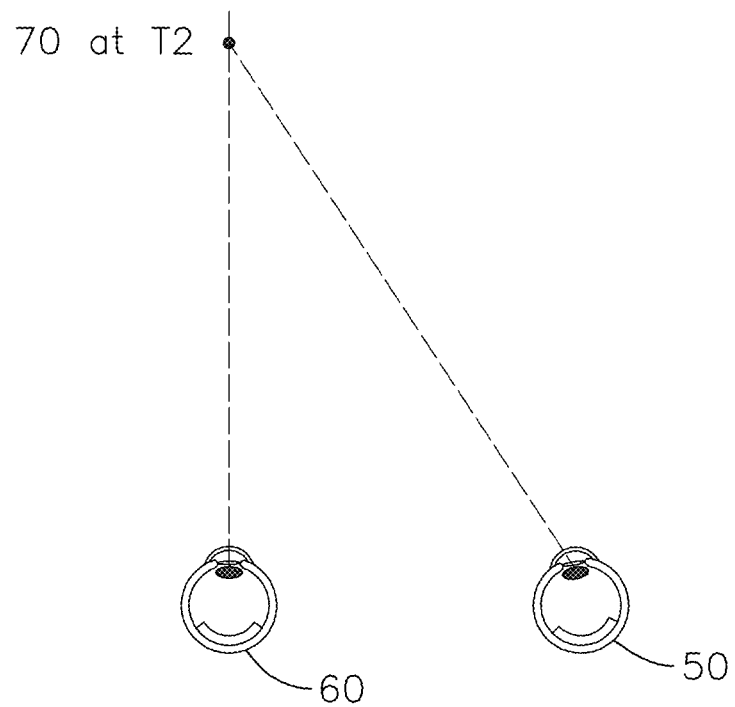
Figure 7A:
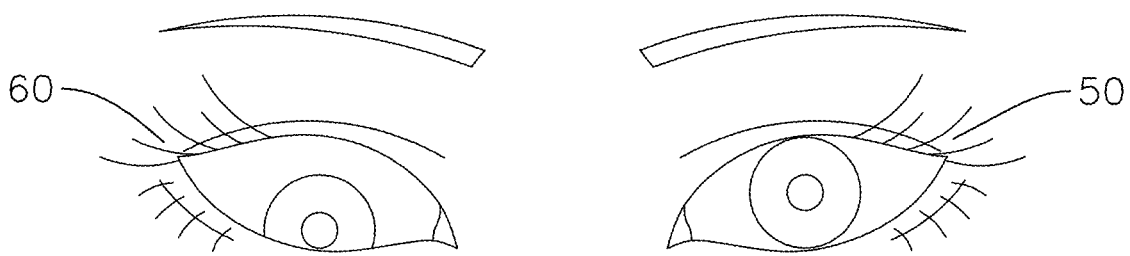
FIGS. 7A-7D are schematic diagrams illustrating examples of abnormal eyes in accordance with the present invention.
Figure 7B:
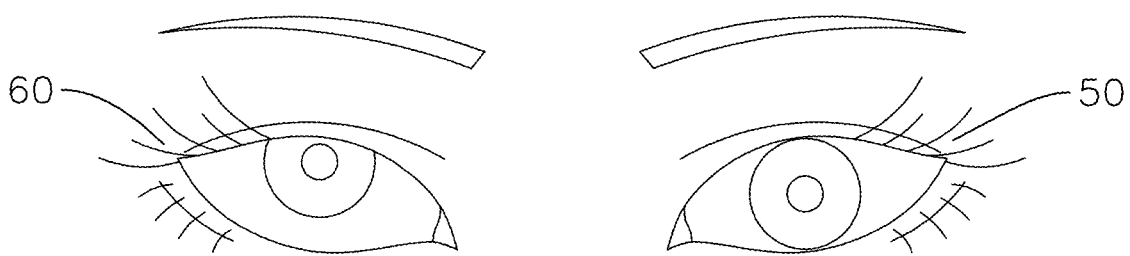
Figure 7C:
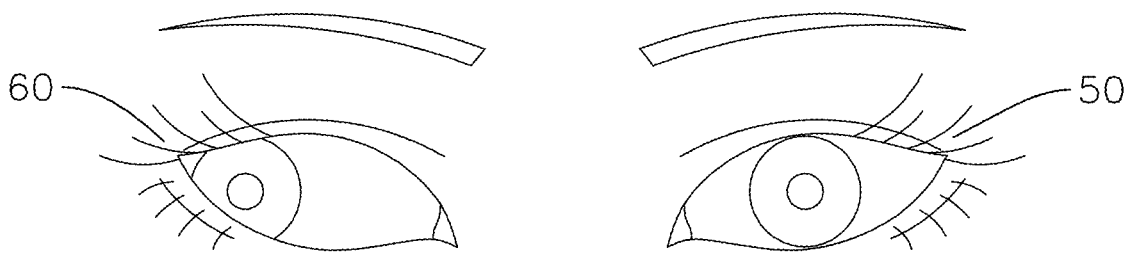
Figure 7D:
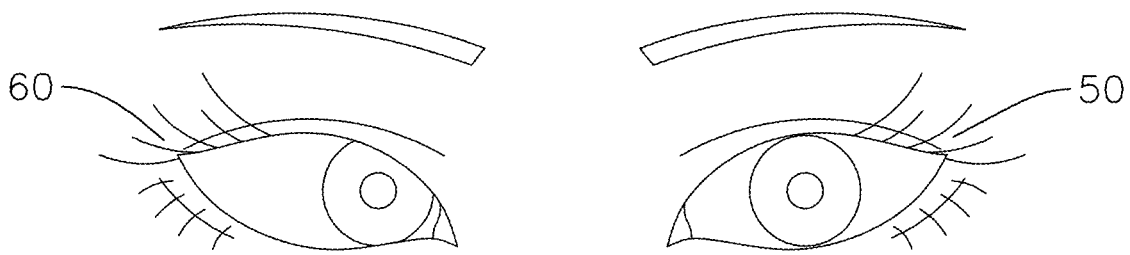

To avoid complication, FIGS. 4 and 5A-5C do not demonstrate the movement of the pupils to follow the movement of the first virtual object 70. FIGS. 6A-6B show that when the first virtual object 70 moves from the first targeted position T1 to the second targeted position T2, the second eye 60 actually moves from left hand side to middle while the first eye 50 remains at about the same location.

Moreover, in order for a viewer to perceive a virtual object at a targeted depth, the system 100, including the eye tracking module 110 and the virtual image module 120, may need to be calibrated first for the viewer. Because every viewer's eyes have different physical characteristics, including interpupillary distance (IPD), the system has to be calibrated specifically for the viewer to assure that with the normal light signals and the adjusted light signals projected into the viewer's eyes, the viewer would perceive the virtual object displayed at the targeted depth.

Figure 8:
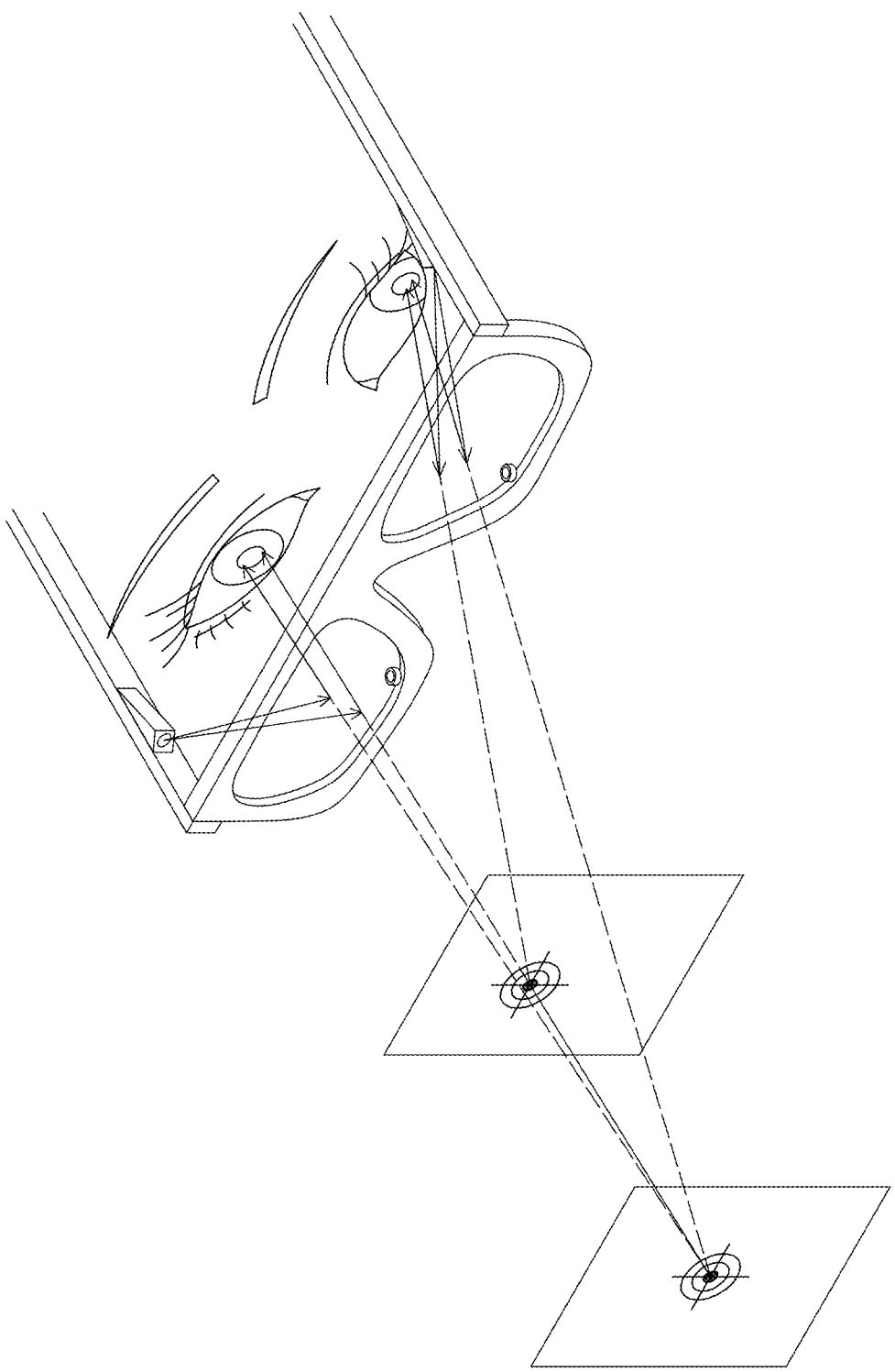
FIG. 8 is a schematic diagram illustrating an embodiment of adjusting the light directions and angles based on the viewer's eye information in accordance with the present invention.

The information of the viewer's eyes, such as pupil location, pupil size, gaze angle (view angle), and vergence angle, from the eye tracking device 110 may be used by the virtual image module 120 to determine the direction and speed of movement of the first virtual image 70. For example, when the weak eye 60 is not able to follow the movement of the first virtual object 70, the virtual image module 120 may move the first virtual object 70 back to a previous position where the viewer's weak eye 60 can still perceive the adjusted image and slow down the movement. The virtual image module 120 may also use the viewer's eye information to determine the direction and angle of the normal light signals and the adjusted light signals to ensure that both eyes, in particular the weak eye 60, receive the light signals and are able to perceive the first virtual object 70. FIGS. 7A-7D respectively show hypotropia (eye turns down), hypertropia (eye turns up), exotropia (eye turns out), and esotropia (eye turns in), the four conditions where the pupil of the weak eye 60 is not able randomly turn in order to coordinate with the pupil of the normal eye 50. Using exotropia as an example as shown in FIG. 8, the virtual image module 120 may respectively adjust the direction and angle of the normal light signals and the adjusted light signals so that the weak eye 60 can perceive the adjusted image.

In some embodiments, the system 100 may be used to correct exotropia and other similar conditions. The virtual image module 120 may display the first virtual object 70 moving slowly toward and/or away from the viewer's weak eye 60. The eye tracking module 110 provides the viewer's eye information such as pupil location, pupil size and view angle to the virtual image module 120 which can accordingly project respectively the normal light signals for the normal eye to perceive the normal image and the adjusted light signals for the weak eye to perceive the adjusted image. Then the virtual image module 120 slightly moves the adjusted image towards the proper direction and away from the weak eye's original location for correction purpose. As a result, the adjusted image perceived by the weak may become slightly blurry and/or the viewer's both eyes perceive double visions (when image fusion fails so that the normal image is separated from the adjusted image). Human brain has the tendency and capability to automatically perform vergence accommodation of both eyes to obtain a clear image of an object. Thus, the viewer may try to turn his/her weak eye slightly to re-obtain a clear image or avoid double vision. When the viewer succeeds, the feedback module 160 may provide a feedback, such as sounds or vibrations, to the viewer. The virtual image module 120 may repeatedly move the adjusted image back and forth to train the weak eye to turn to the proper direction so that the mis-alignment of the viewer's two eyes may be reduced.

Figure 9:
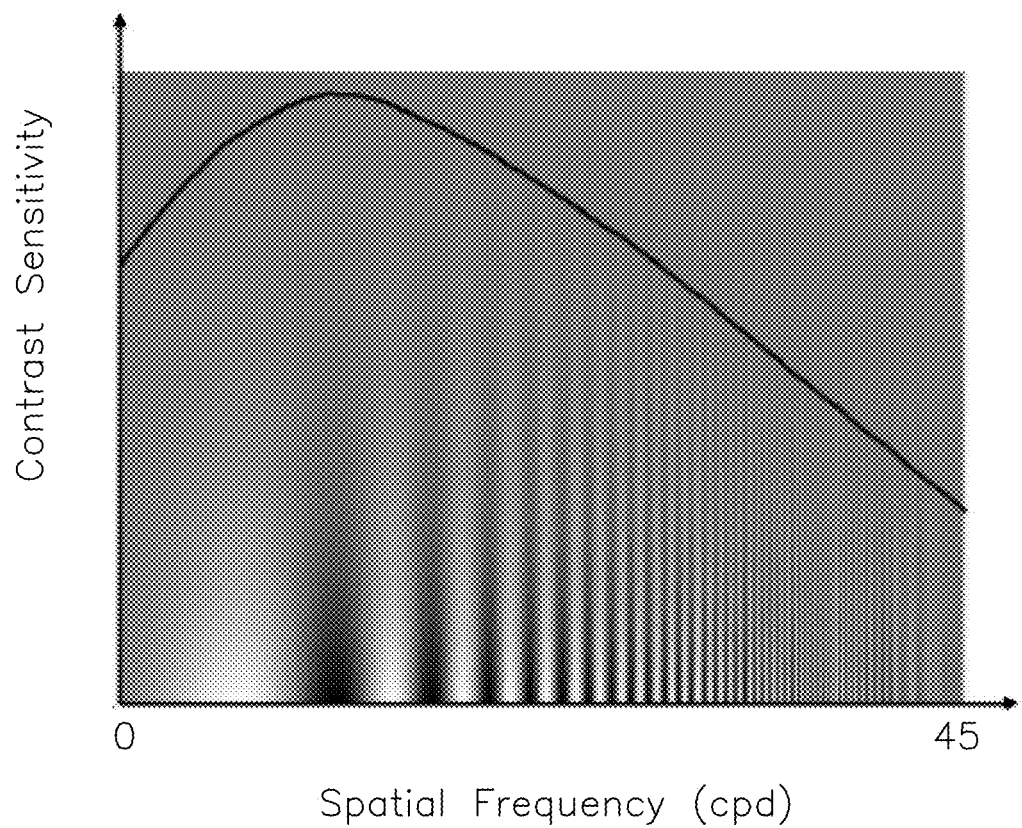
FIG. 9 is a photo illustrating an example of contrast sensitivity function in accordance with the present invention.

To improve the vision of the viewer's weak eye 60, the virtual image module 120 may differentiate the contrast and the spatial frequency of the normal image 122 for the viewer's first eye 50 from those of the adjusted image 124 for the viewer's second eye 60. Specifically, the virtual image module 120 is configured to generate the adjusted image 122 having higher contrast or lower spatial frequency than the corresponding normal image 124. The virtual image module 120 may select an appropriate contrast and spatial frequency for the adjusted image 122 at least in part based on the weak eye's contrast sensitivity function so that the viewer's weak eye 60 receives stronger stimulation and clearly perceives the adjusted image 124. Each eye has its own contrast sensitivity function a sample of which is shown in FIG. 9. The virtual image module 120 may adjust the contrast and/or spatial frequency of the normal image 122 so that the normal eye 50 receives less stimulation and perceives the normal image 122 with lower contrast and height spatial frequency. As a result, the weak eye 60 is exercised and trained more to contribute to the viewer's vision. Without the system 100 for improving the binocular vision, the viewer would avoid exercising his/her weak eye which cannot provide clear image and thus the weaker eye 60 becomes further weaker or even blind.

Contrast is the difference in luminance or colour that makes an object (or its representation in an image or display) distinguishable. In visual perception of the real world, contrast is determined by the difference in the colour and brightness of the object and other objects within the same field of view. Through a contrast sensitivity exam, a contrast sensitivity curve (also known as contrast sensitivity function) of a viewer's eye can be plotted, with angular frequency on the horizontal, and contrast threshold on the vertical axis. Images shown to the viewer for such exam have varying contrast on the vertical coordinate and angular frequency on the horizontal coordinate. Parallel bars of varying width and contrast, known as sine-wave gratings, are sequentially viewed by the viewer to plot the curve. The width of the bars and their distance apart represent angular frequency, measured in cycles per degree. Studies have demonstrated that medium-level angular frequency, approximately 5-7 cycles per degree, is optimally detected by most individuals, compared with low- or high-level angular frequencies.

The contrast threshold can be defined as the minimum contrast that can be resolved by the patient.

As described above, the virtual image module 120 may project the adjusted image 124 to the viewer's weak eye 60 with higher contrast and/or lower spatial frequency. Below are some examples. For higher contrast, the adjusted image 124 has higher luminance than the normal image 122; the adjusted image 124 is colorful while the normal image 122 is in black and white (with gray levels); the adjusted image 124 is in green color while the normal image 122 is in red color. For lower spatial frequency, the adjusted image 124 is the foreground view of an image while the normal image 122 is the background view of the same image. The virtual image module 120 may first divide an image into a lower spatial frequency portion and a higher spatial image portion, and then projecting the lower spatial frequency portion, such as the foreground view, to the weak eye 60 and the higher spatial frequency portion, such as the background view, to the normal eye 50. In this situation, the adjusted image 124 (lower spatial frequency portion) is sufficiently related to the normal image 122 (higher spatial frequency portion) for binocular fusion because they come from the same image although the adjusted image and the normal image look different because of different patterns and spatial frequencies.

Figure 10:
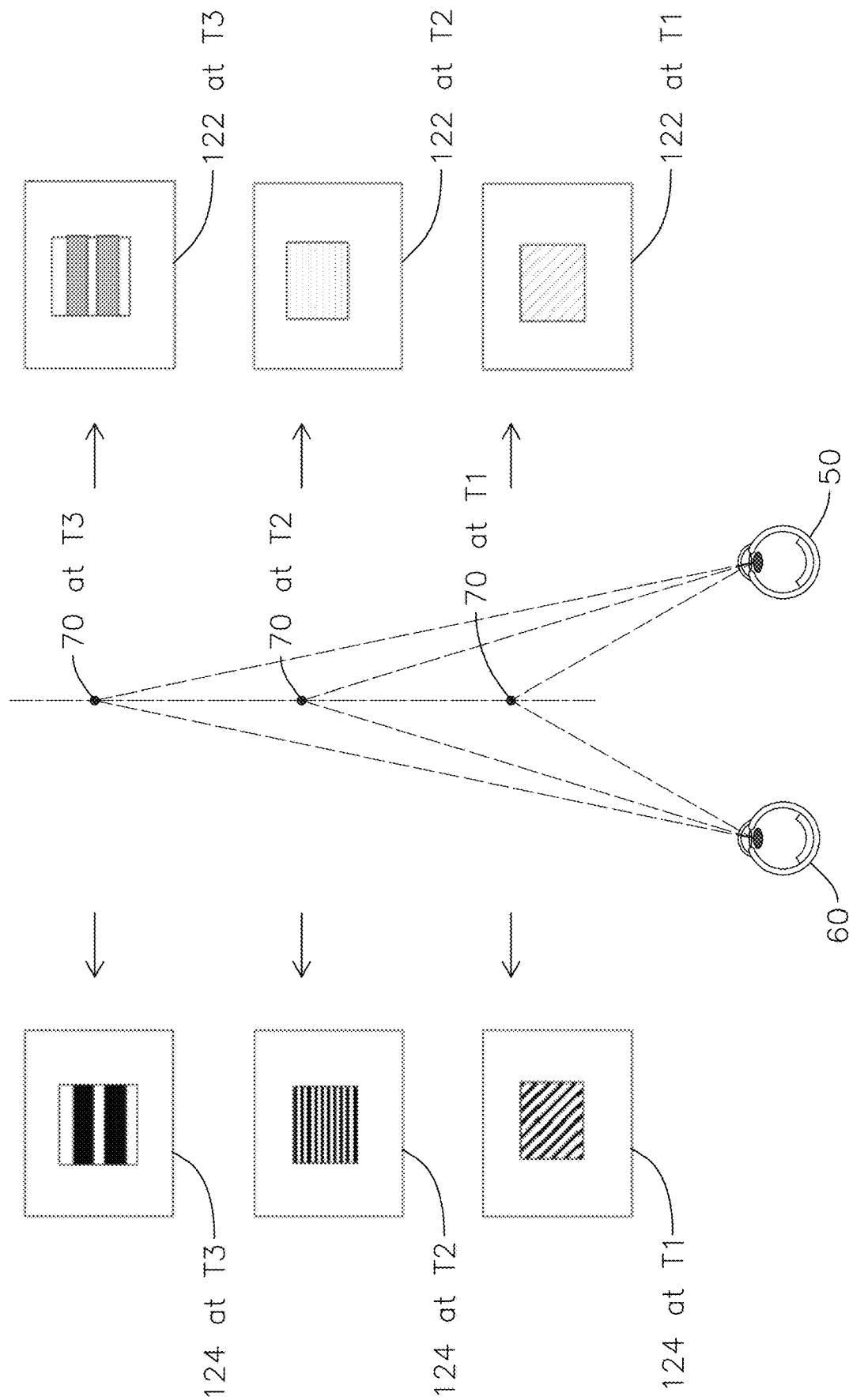
FIG. 10 is a schematic diagram illustrating an embodiment of adjusting spatial frequency of a virtual object because of different displaying depths in accordance with the present invention.

As shown in FIG. 10, while the virtual image module 120 moves the first virtual object through different positions with different targeted depths, the spatial frequency of the first virtual object 70 may be adjusted according to the targeted depths. When the same virtual object is moved to a position with a greater depth, the spatial frequency of exactly the same virtual object automatically increases because it is further away from the viewer. As a result, the weak eye 60 may have a difficulty to clearly perceive the virtual object when it moves away from the viewer. In order for the viewer's weak eye to maintain clear perception of the adjusted image, the virtual image module may adjust the spatial frequency of the first virtual object, including both the adjusted image and the normal image, so that the first virtual object has a lower spatial frequency when the first virtual object is displayed at a greater depth. As shown in FIG. 10, when the first virtual object 70 is moved to a position with a greater depth, for example from the first targeted position T1 to the second targeted position T2 and then to the third targeted position T3, the spatial frequency of the first virtual object 70 is decreased to overcome the above problem.

The system 100 for improving binocular vision may further include a VEP measuring module 130 to measure a visual evoked potential (VEP) of the viewer's eyes. VEP measures the electrical signal generated at the visual cortex in response to visual stimulation. VEP refers to electrical potentials recorded from scalp overlying visual cortex that have been extracted from the electroencephalogram by signal averaging. Usually the recording electrode is placed on the midline of the occipital scalp at the back of the head. VEPs are used to quantify the functional integrity of the optic nerves, visual pathways from eyes to the visual cortex of the brain, and occipital cortex. Thus VEP provides important information for the virtual image module to adjust the manner of displaying the first virtual object, including the speed and direction of moving the first virtual object 70, and the contrast and the spatial frequency of the adjusted image 124.

The VEP measuring module 130 may constantly measure the VEP of either or both the viewer's eyes and provide such information to the virtual image module. The measurement may be conducted frequently on a real time manner or once a while after the viewer's weak eye shows some improvement. The VEP may reflect the extent the viewer's weak eye can perceive the adjusted image. The VEP may also reflect whether the viewer's eyes, in particular the weak eye, fixate during a time period. For example, when the viewer's weak eye loses fixation and makes some moves, the VEP of the weak eye may fluctuate. Nevertheless, when the viewer's weak eye maintains fixation, the VEP of the weak eye may remain about the same. Thus, The virtual image module may display the first virtual object, including selecting an appropriate contrast and spatial frequency, and the direction and speed of movement of the first virtual object, based on the VEP of either or both the viewer's eyes.

The virtual image module 120 may display the first virtual object 70 based on the VEP of either or both the viewer's eyes even if the system does not include the VEP measuring module. A separate VEP measuring module may communicate the VEP of either or both the viewer's eyes to the system via wired or wireless manner. The wireless manner may include WiFi, bluetooth, near field communication (NFC), internet, telecommunication, radio frequency (RF), etc. The VEP of either or both the viewer's eyes may also be input to the system via a user interface of the system, for example a keyboard and a mouse.

The system 100 for improving binocular vision begins with projecting the adjusted image with appropriate contrast and spatial frequency to exercise the viewer's weak eye with sufficiently strong stimulation. When the viewer's weak eye becomes stronger, the virtual image module may gradually lower the contrast and/or increase the spatial frequency of the adjusted image while the viewer's weak eye can still clearly perceive the adjusted image until the adjusted image becomes very close to the normal image. At the same time, the moving of the first virtual object from the first position to the second position trains the viewer's weak eye to follow the movement and perceive the depth of the first virtual object. When the viewer is able to practice fixation, the virtual image module may display the first virtual object at the viewer's fixation location and fixation depth (collectively "fixation position") provided by the eye tracking module. When the viewer moves its fixation from a first fixation location and a first fixation depth (collectively the "first fixation position" or "F1") to a second fixation location and a second fixation depth (collectively the "second fixation position" or "F2"), the virtual image module moves the first virtual image according to the viewer's fixation.

Figure 11A:
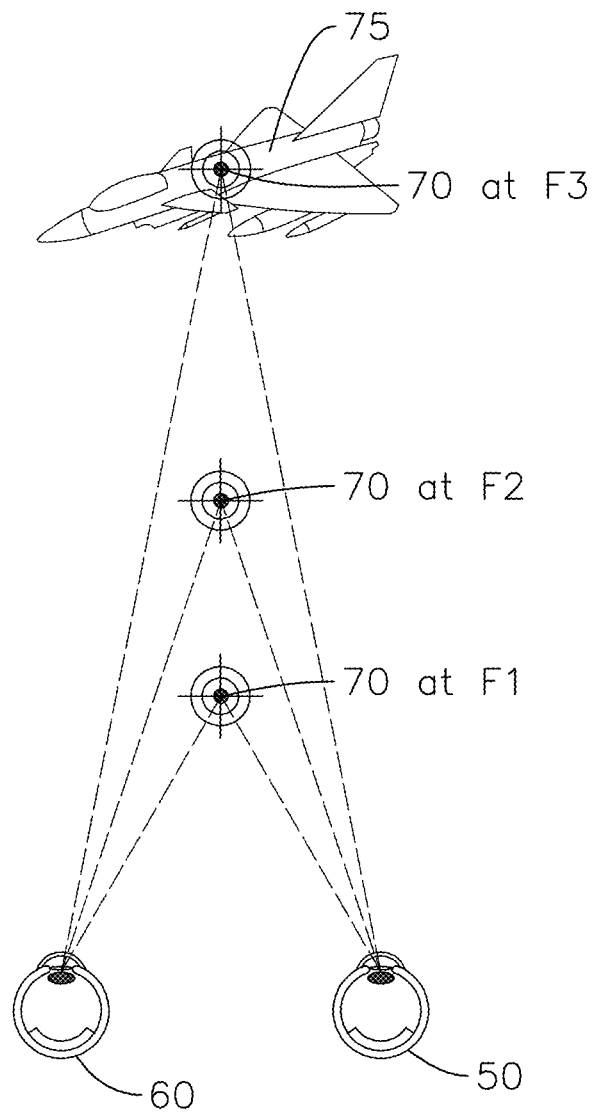
FIGS. 11A and 11B are schematic diagrams illustrating an embodiment of moving a first virtual object based on fixation of a viewer's eyes to superimpose on a second virtual object in accordance with the present invention.
Figure 11B:
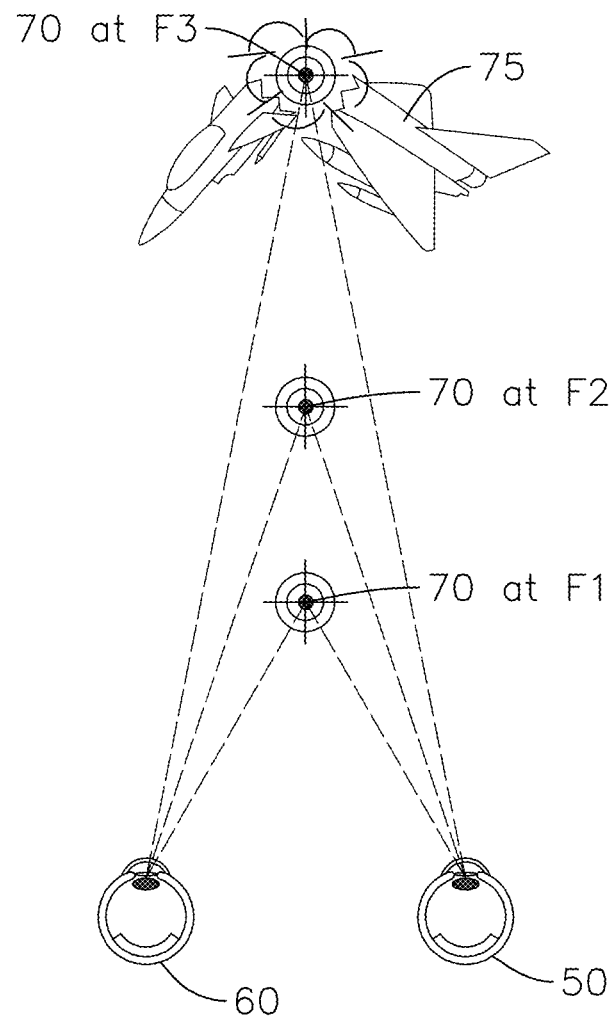

Employing the above mechanism of moving the first virtual object according to the movement of the viewer's fixation, many games may be designed to train the viewer's capability of fixation and image fusion. The virtual image module may display a second virtual object 75 at a predetermined location and a predetermined depth. When the viewer moves his/her fixation to cause the first virtual object to move within a predetermined spatial range of the second virtual object or to superimpose on the second virtual object for a predetermined period of time, the second virtual object is altered to interact with the first virtual object. In a first example as shown in FIGS. 11A and 11B, the first virtual object 70 is an aiming cursor that is moved according to the viewer's fixation, from F1 to F2 to F3, and the second virtual object 75 is a shooting target such as an air fighter. When the first virtual object 70, e.g. aiming cursor, is moved to superimpose on the second virtual object 75, e.g. an air fighter, the second virtual object 75 is altered to display an explosion to provide a feedback to the viewer that the second virtual object is hit and destroyed. In a second example, the first virtual object is a bowling ball, and the second virtual object is a set of bowling pins. When the viewer moves its fixation to cause the bowling ball to superimpose on (to hit) the set of bowling pins. The virtual image module displays that some of all of the bowling pins fall to respond to the hit and to provide a feedback to the viewer. In a third example, the first virtual object is a "snake" comprising a plurality of blocks, which is moved by the viewer's fixation to "eat" additional blocks, the second virtual objects. These blocks may be formed by combining various patterns with different contrasts and spatial frequencies. As a result, the moving "snake" can enhance the stimulation of the visual cortex of the viewer and promote better training result.

The system 100 may interact with the reality. Similar to the above shooting game example, the viewer may move his/her fixation to cause the first virtual object such as an aiming cursor, to move within a predetermined spatial range of a real object, such as a teapot on a table, for a predetermined period of time. Then the virtual image module may display a virtual object, such as fireworks, as a feedback, to show the viewer that the real object is successfully hit. The feedback conditions and other parameters, such as the predetermined spatial range, the predetermined period of time, the virtual object for feedback, of the training game may be set in advance by the viewer or a trainer. Thus, the training game may be set to require that the aiming cursor has to superimpose on the real object for 3 seconds.

The system 100 may further include a real object measuring module 150 to measure a location and a depth of a real object, such as a clock and a picture hung on a wall. The real object may be a moving object, such as a remote control airplane and a dog. The real object measuring module 150 configured to be connected to other modules of the system may continuously or periodically measure the location and depth of the real object relative to the object measuring module (or the viewer), and communicate the associated information to the virtual image module to determine whether a feedback condition is satisfied. For example, upon receipt of such information, the control module 125 may calculate the spatial distance between the first virtual object, such as an aiming cursor, and the real object and determine whether the first virtual object is superimposed on the real object. The distance between the real object and the real object measuring module 150 (or the viewer's eyes) may change along the time. In one situation, the real object 105, such as a remote control airplane, may move during the game. In another situation, the system 100 may be worn by a viewer, such as a patient, and the viewer may move his/her head during the game. Thus, the distance between the real object and the viewer's eye needs to be measured and calculated in order to precisely determine whether a feedback condition is satisfied. The real object measuring module 150 may include a gyroscope, indoor/outdoor global positioning system (GPS) and a distance measurement components (e.g. emitters and sensors) to precisely track the variation of the location and depth of the real object.

In addition to displaying a virtual object, such as exploded airplane, as a feedback, the system 100 may provide other types of feedbacks, such as sounds and vibrations. Thus, the system 100 may further include a feedback module 160 to generate a feedback to a viewer when a feedback condition is satisfied. The feedback module may be a speaker to provide sounds, such as explosion sounds or a vibration generator to provide various types of vibrations. The type of feedback can be set up in by the viewer or the trainer through the user interface 140.

The virtual image module 120 and the method of generating virtual objects 70, 75 at a predetermined locations and depths as well as the method of moving the virtual objects as desired are discussed in details below. The PCT international application PCT/US20/59317, filed on Nov. 6, 2020, titled "SYSTEM AND METHOD FOR DISPLAYING AN OBJECT WITH DEPTHS" is incorporated herein by reference at its entirety.

Figure 12:
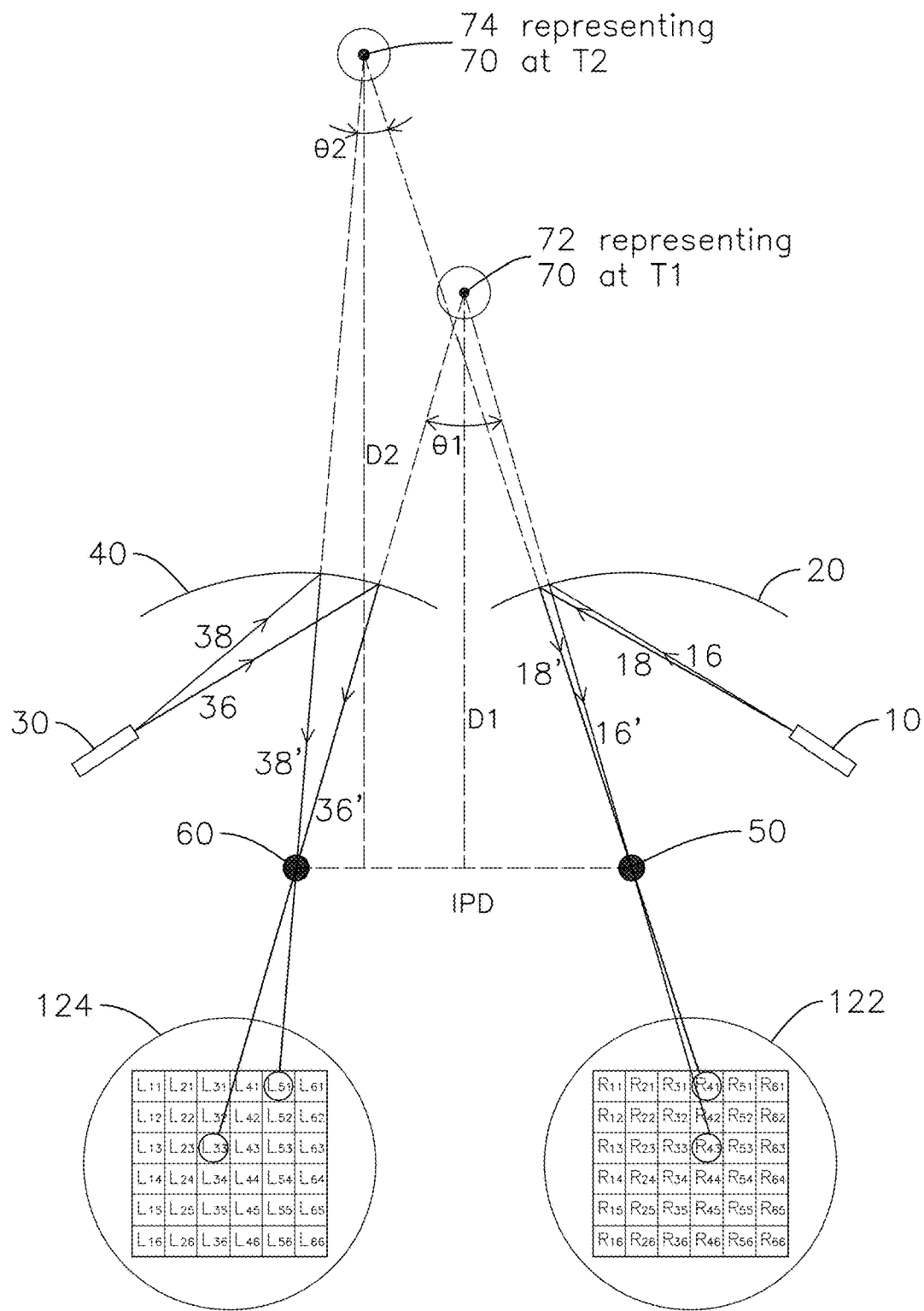
FIG. 12 is a schematic diagram illustrating a relationship between a virtual binocular pixel and the corresponding pair of the normal pixel and adjusted pixel in accordance with the present invention.

As shown in FIG. 12, the viewer perceives the first virtual object of the tennis ball 70 in the area C in front of the viewer. The image of the tennis ball virtual object 70 displayed at a first targeted position T1 (with depth D1) is represented a first virtual binocular pixel 72 (its center point) and when the first virtual object 70 moves to a second targeted position T2 (with depth D2), it is represented by the second virtual binocular pixel 74. The first angle between the first redirected normal light signal 16' (the first normal light signal) and the corresponding first redirected adjusted light signal (the first adjusted light signal) 36' is θ1. The first depth D1 is related to the first angle θ1. In particular, the first depth of the first virtual binocular pixel of the first virtual object 70 can be determined by the first angle θ1 between the light path extensions of the first redirected normal light signal and the corresponding first redirected adjusted light signal. As a result, the first depth D1 of the first virtual binocular pixel 72 can be calculated approximately by the following formula:

$$\operatorname{Tan}\left(\frac{\theta}{2}\right) = \frac{IPD}{2D}$$

The distance between the normal pupil 52 and the adjusted pupil 62 is interpupillary distance (IPD). Similarly, the second angle between the second redirected normal light signal (the second normal light signal) 18' and the corresponding second redirected adjusted light signal (the second adjusted light signal) 38' is θ2. The second depth D2 is related to the second angle θ2. In particular, the second depth D2 of the second virtual binocular pixel 74 of the virtual object 70 at T2 can be determined approximately by the second angle θ2 between the light path extensions of the second redirected normal light signal and the corresponding second redirected adjusted light signal by the same formula. Since the second virtual binocular pixel 74 is perceived by the viewer to be further away from the viewer (i.e. with larger depth) than the first virtual binocular pixel 72, the second angle θ2 is smaller than the first angle θ1.

Furthermore, although the redirected normal light signal 16' for NLS_2 and the corresponding redirected adjusted light signal 36' for ALS_2 together display a first virtual binocular pixel 72 with the first depth D1. The redirected normal light signal 16' for NLS_2 may present an image of the same or different view angle from the corresponding redirected adjusted light signal 36' for ALS_2. In other words, although the first angle θ1 determines the depth of the first virtual binocular pixel 72, the redirected normal light signal 16' for NLS_2 may be or may not be a parallax of the corresponding redirected adjusted light signal 36' for ALS_2. Thus, the intensity of red, blue, and green (RBG) color and/or the brightness of the normal light signal and the adjusted light signal may be approximately the same or slightly different, because of the shades, view angle, and so forth, to better present some 3D effects.

As described above, the multiple normal light signals are generated by the normal light signal generator 10, redirected by the normal combiner 20, and then directly scanned onto the normal retina to form a normal image 122 (normal retina image 86 in FIG. 13) on the normal retina. Likewise, the multiple adjusted light signals are generated by adjusted light signal generator 30, redirected by the adjusted combiner 40, and then scanned onto the adjusted retina to form an adjusted image 124 (adjusted retina image 96 in FIG. 13) on the adjusted retina. In an embodiment shown in FIG. 12, a normal image 122 contains 36 normal pixels in a 6×6 array and an adjusted image 124 also contains 36 adjusted pixels in a 6×6 array. In another embodiment, a normal image 122 may contain 921,600 normal pixels in a 1280×720 array and an adjusted image 124 may also contain 921,600 adjusted pixels in a 1280×720 array. The virtual image module 120 is configured to generate multiple normal light signals and corresponding multiple adjusted light signals which respectively form the normal image 122 on the normal retina and adjusted image 124 on the adjusted retina. As a result, the viewer perceives a virtual object with specific depths in the area C because of image fusion.

With reference to FIG. 12, the first normal light signal 16 from the normal light signal generator 10 is received and reflected by the normal combiner 20. The first redirected normal light signal 16', through the normal pupil 52, arrives the normal retina of the viewer to display the normal retina pixel R43. The corresponding adjusted light signal 36 from the adjusted light signal generator 30 is received and reflected by the adjusted combiner 40. The first redirected light signal 36', through the adjusted pupil 62, arrives the adjusted retina of the viewer to display the adjusted retina pixel L33. As a result of image fusion, a viewer perceives the first virtual object 70 at the first depth D1 determined by the first angle of the first redirected normal light signal and the corresponding first redirected adjusted light signal. The angle between a redirected normal light signal and a corresponding adjusted light signal is determined by the relative horizontal distance of the normal pixel and the adjusted pixel. Thus, the depth of a virtual binocular pixel is inversely correlated to the relative horizontal distance between the normal pixel and the corresponding adjusted pixel forming the virtual binocular pixel. In other words, the deeper a virtual binocular pixel is perceived by the viewer, the smaller the relative horizontal distance at X axis between the normal pixel and adjusted pixel forming such a virtual binocular pixel is. For example, as shown in FIG. 12, the second virtual binocular pixel 74 is perceived by the viewer to have a larger depth (i.e. further away from the viewer) than the first virtual binocular pixel 72. Thus, the horizontal distance between the second normal pixel and the second adjusted pixel is smaller than the horizontal distance between the first normal pixel and the first adjusted pixel on the retina images 122, 124. Specifically, the horizontal distance between the second normal pixel R41 and the second adjusted pixel L51 forming the second virtual binocular pixel 74 is four-pixel long. However, the distance between the first normal pixel R43 and the first adjusted pixel L33 forming the first virtual binocular pixel 72 is six-pixel long.

Figure 13:
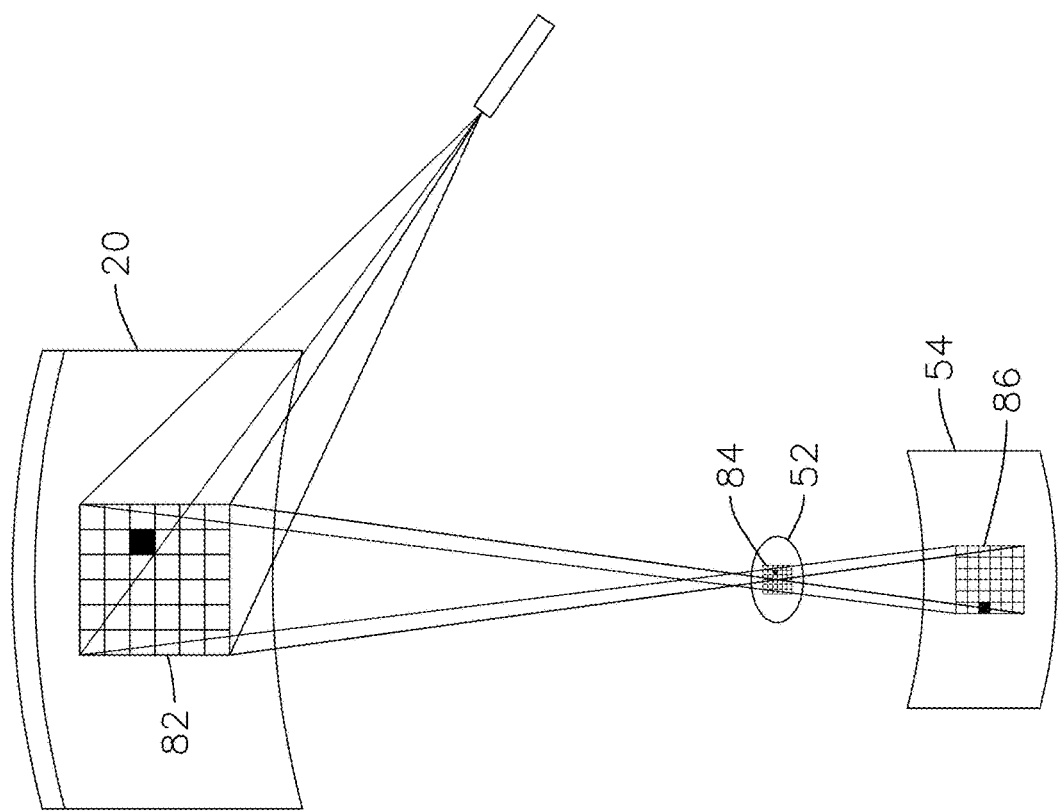
FIG. 13 is a schematic diagram illustrating the light path from a light signal generator to a combiner, and to a retina of a viewer in accordance with the present invention.
Figure 13:
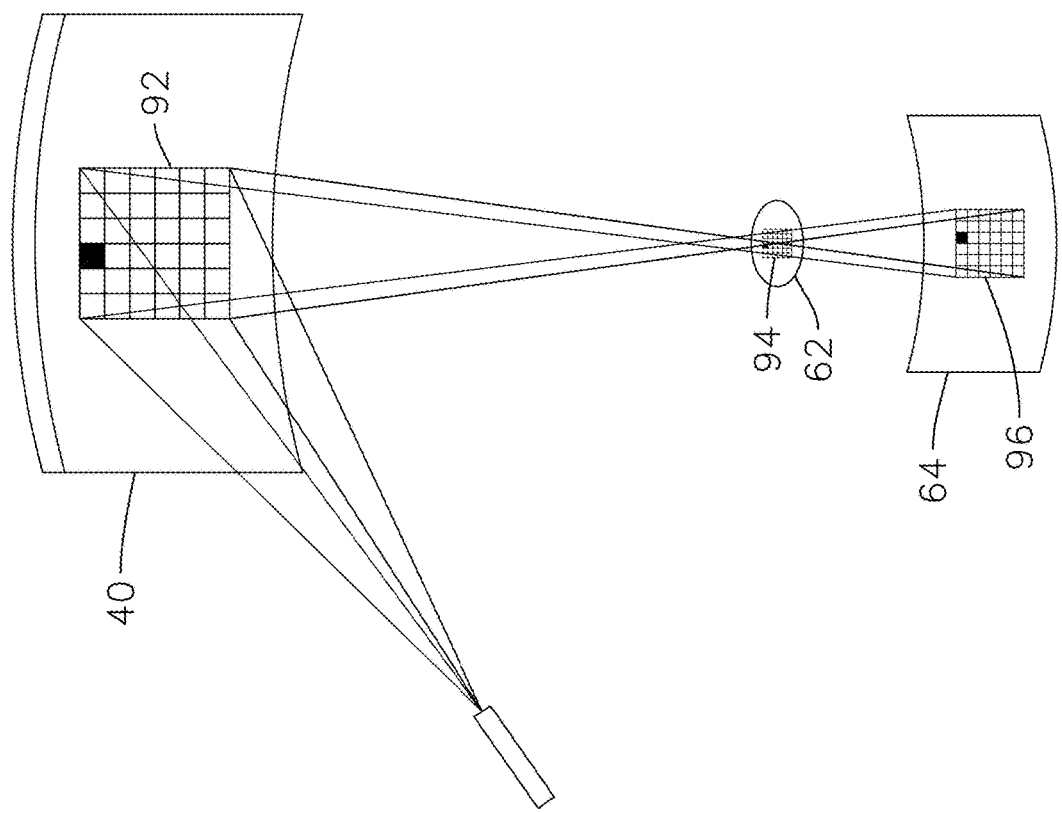

In one embodiment shown in FIG. 13, the light paths of multiple normal light signals and multiple adjusted light signals from light signal generators to retinas are illustrated. The multiple normal light signals generated from the normal light signal generator 10 are projected onto the normal combiner 20 to form a normal combiner image (RSI) 82. These multiple normal light signals are redirected by the normal combiner 20 and converge into a small normal pupil image (RPI) 84 to pass through the normal pupil 52, and then eventually arrive the normal retina 54 to form a normal retina image (RRI) 86 (normal image 122). Each of the RSI, RPI, and RRI comprises i×j pixels. Each normal light signal NLS(i,j) travels through the same corresponding pixels from RSI(i,j), to RPI(i,j), and then to RRI(x,y). For example NLS(5,3) travels from RSI(5,3), to RPI(5,3) and then to RRI(2,4) Likewise, the multiple adjusted light signals generated from the adjusted light signal generator 30 are projected onto the adjusted combiner 40 to form a adjusted combiner image (LSI) 92. These multiple adjusted light signals are redirected by the adjusted combiner 40 and converge into a small adjusted pupil image (LPI) 94 to pass through the adjusted pupil 62, and then eventually arrive the adjusted retina 64 to form an adjusted retina image (LRI) 96 (adjusted image 124). Each of the LSI, LPI, and LRI comprises i×j pixels. Each adjusted light signal ALS(i,j) travels through the same corresponding pixels from LCI(i,j), to LPI(i,j), and then to LRI(x,y). For example ALS(3,1) travels from LCI(3,1), to LPI(3,1) and then to LRI(4,6). The (0, 0) pixel is the top and left most pixel of each image. Pixels in the retina image is left-right inverted and top-bottom inverted to the corresponding pixels in the combiner image. Based on appropriate arrangements of the relative positions and angles of the light signal generators and combiners, each light signal has its own light path from a light signal generator to a retina. The combination of one normal light signal displaying one normal pixel on the normal retina and one corresponding adjusted light signal displaying one adjusted pixel on the adjusted retina forms a virtual binocular pixel with a specific depth perceived by a viewer. Thus, a virtual binocular pixel in the space can be represented by a pair of normal retina pixel and adjusted retina pixel or a pair of normal combiner pixel and adjusted combiner pixel.

A virtual object perceived by a viewer in area C may include multiple virtual binocular pixels but is represented by one virtual binocular pixel in this disclosure. To precisely describe the location of a virtual binocular pixel in the space, each location in the space is provided a three dimensional (3D) coordinate, for example XYZ coordinate. Other 3D coordinate system can be used in another embodiment. As a result, each virtual binocular pixel has a 3D coordinate—a horizontal direction, a vertical direction, and a depth direction. A horizontal direction (or X axis direction) is along the direction of interpupillary line. A vertical direction (or Y axis direction) is along the facial midline and perpendicular to the horizontal direction. A depth direction (or Z axis direction) is normal to the frontal plane and perpendicular to both the horizontal and vertical directions. The horizontal direction coordinate and vertical direction coordinate are collectively referred to as the location in the present invention.

Figure 14:
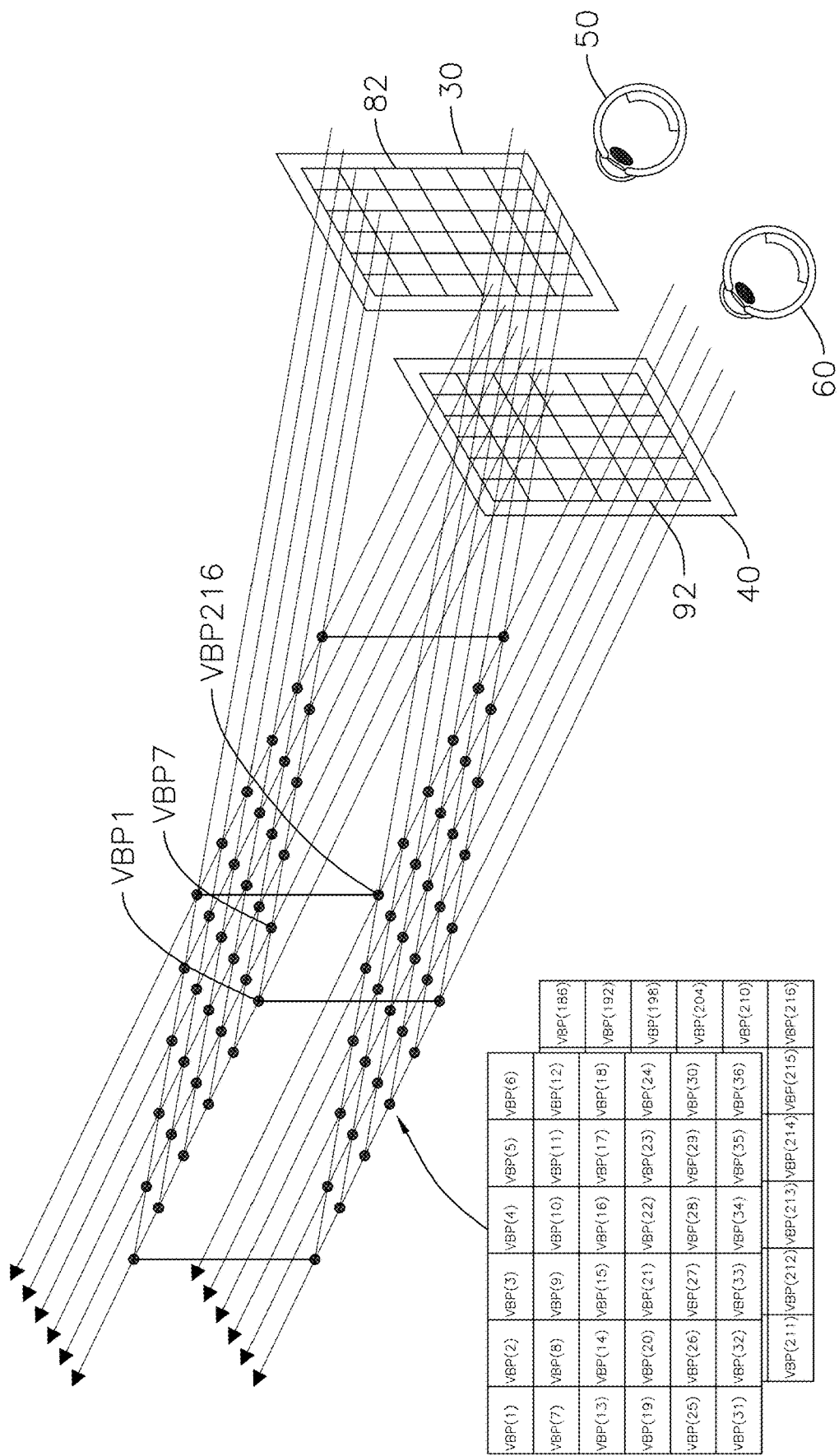
FIG. 14 is a schematic diagram illustrating the virtual binocular pixels formed by normal light signals and adjusted light signals in accordance with the present invention.

FIG. 14 illustrates the relationship between pixels in the normal combiner image, pixels in the adjusted combiner image, and the virtual binocular pixels. As described above, pixels in the normal combiner image are one to one correspondence to pixels in the normal retina image (normal pixels). Pixels in the adjusted combiner image are one to one correspondence to pixels in the adjusted retina image (adjusted pixels). However, pixels in the retina image is left-right inverted and top-bottom inverted to the corresponding pixels in the combiner image. For a normal retina image comprising 36 (6×6) normal pixels and an adjusted retina image comprising 36 (6×6) adjusted pixels, there are 216 (6×6×6) virtual binocular pixels (shown as a dot) in the area C assuming all light signals are within FOV of both eyes of the viewer. The light path extension of one redirected normal light signal intersects the light path extension of each redirected adjusted light signal on the same row of the image. Likewise, the light path extension of one redirected adjusted light signal intersects the light path extension of each redirected normal light signal on the same row of the image. Thus, there are 36 (6×6) virtual binocular pixels on one layer and 6 layers in the space. There is usually a small angle between two adjacent lines representing light path extensions to intersect and form virtual binocular pixels although they are shown as parallel lines in the FIG. 14. A normal pixel and a corresponding adjusted pixel at approximately the same height of each retina (i.e. the same row of the normal retina image and adjusted retina image) tend to fuse earlier. As a result, normal pixels are paired with adjusted pixels at the same row of the retina image to form virtual binocular pixels.

As shown in FIG. 15, a look-up table is created to facilitate identifying the normal pixel and adjusted pixel pair for each virtual binocular pixel. For example, 216 virtual binocular pixels, numbering from 1 to 216, are formed by 36 (6×6) normal pixels and 36 (6×6) adjusted pixels. The first ($1^{st}$) virtual binocular pixel VBP(1) represents the pair of normal pixel RRI(1,1) and adjusted pixel LRI(1,1). The second (2') virtual binocular pixel VBP(2) represents the pair of normal pixel RRI(2,1) and adjusted pixel LRI(1,1). The seventh ($7^{th}$) virtual binocular pixel VBP(7) represents the pair of normal pixel RRI(1,1) and adjusted pixel LRI(2, 1). The thirty-seventh ($37^{th}$) virtual binocular pixel VBP(37) represents the pair of normal pixel RRI(1,2) and adjusted pixel LRI(1,2). The two hundred and sixteenth ($216^{th}$) virtual binocular pixel VBP(216) represents the pair of normal pixel RRI(6,6) and adjusted pixel LRI(6,6). Thus, in order to display a specific virtual binocular pixel of a virtual object in the space for the viewer, it is determined which pair of the normal pixel and adjusted pixel can be used for generating the corresponding normal light signal and adjusted light signal. In addition, each row of a virtual binocular pixel on the look-up table includes a pointer which leads to a memory address that stores the perceived depth (z) of the VBP and the perceived position (x,y) of the VBP. Additional information, such as scale of size, number of overlapping objects, and depth in sequence depth etc., can also be stored for the VBP. Scale of size may be the relative size information of a specific VBP compared against a standard VBP. For example, the scale of size may be set to be 1 when the virtual object is displayed at a standard VBP that is 1 m in front of the viewer. As a result, the scale of size may be set to be 1.2 for a specific VBP that is 90 cm in front of the viewer. Likewise, when the scale of size may be set to be 0.8 for a specific VBP that is 1.5 m in front of the viewer. The scale of size can be used to determine the size of the virtual object for displaying when the virtual object is moved from a first depth to a second depth. Scale of size may be the magnification in the present invention. The number of overlapping objects is the number of objects that are overlapped with one another so that one object is completely or partially hidden behind another object. The depth in sequence provides information about sequence of depths of various overlapping images. For example, 3 images overlapping with each other. The depth in sequence of the first image in the front may be set to be 1 and the depth in sequence of the second image hidden behind the first image may be set to be 2. The number of overlapping images and the depth in sequence may be used to determine which and what portion of the images need to be displayed when various overlapping images are in moving.

The look up table may be created by the following processes. At the first step, obtain an individual virtual map based on his/her IPD, created by the virtual image module during initiation or calibration, which specify the boundary of the area C where the viewer can perceive a virtual object with depths because of the fusion of normal retina image and adjusted retina image. At the second step, for each depth at Z axis direction (each point at Z-coordinate), calculate the convergence angle to identify the pair of normal pixel and adjusted pixel respectively on the normal retina image and the adjusted retina image regardless of the X-coordinate and Y-coordinate location. At the third step, move the pair of normal pixel and adjusted pixel along X axis direction to identify the X-coordinate and Z-coordinate of each pair of normal pixel and adjusted pixel at a specific depth regardless of the Y-coordinate location. At the fourth step, move the pair of normal pixel and adjusted pixel along Y axis direction to determine the Y-coordinate of each pair of normal pixel and adjusted pixel. As a result, the 3D coordinate system such as XYZ of each pair of normal pixel and adjusted pixel respectively on the normal retina image and the adjusted retina image can be determined to create the look up table. In addition, the third step and the fourth step are exchangeable.

The light signal generator 10 and 30 may use laser, light emitting diode ("LED") including mini and micro LED, organic light emitting diode ("OLED"), or superluminescent diode ("SLD"), LCoS (Liquid Crystal on Silicon), liquid crystal display ("LCD"), or any combination thereof as its light source. In one embodiment, the light signal generator 10 and 30 is a laser beam scanning projector (LBS projector) which may comprise the light source including a red color light laser, a green color light laser, and a blue color light laser, a light color modifier, such as Dichroic combiner and Polarizing combiner, and a two dimensional (2D) adjustable reflector, such as a 2D electromechanical system ("MEMS") mirror. The 2D adjustable reflector can be replaced by two one dimensional (1D) reflector, such as two 1D MEMS mirror. The LBS projector sequentially generates and scans light signals one by one to form a 2D image at a predetermined resolution, for example 1280×720 pixels per frame. Thus, one light signal for one pixel is generated and projected at a time towards the combiner 20, 40. For a viewer to see such a 2D image from one eye, the LBS projector has to sequentially generate light signals for each pixel, for example 1280×720 light signals, within the time period of persistence of vision, for example $1/18$ second. Thus, the time duration of each light signal is about 60.28 nanosecond.

In another embodiment, the light signal generator 10 and 30 may be a digital light processing projector ("DLP projector") which can generate a 2D color image at one time. Texas Instrument's DLP technology is one of several technologies that can be used to manufacture the DLP projector. The whole 2D color image frame, which for example may comprise 1280×720 pixels, is simultaneously projected towards the combiners 20, 40.

The combiner 20, 40 receives and redirects multiple light signals generated by the light signal generator 10, 30. In one embodiment, the combiner 20, 40 reflects the multiple light signals so that the redirected light signals are on the same side of the combiner 20, 40 as the incident light signals. In another embodiment, the combiner 20, 40 refracts the multiple light signals so that the redirected light signals are on the different side of the combiner 20, 40 from the incident light signals. When the combiner 20, 40 functions as a refractor. The reflection ratio can vary widely, such as 20%-80%, in part depending on the power of the light signal generator. People with ordinary skill in the art know how to determine the appropriate reflection ratio based on characteristics of the light signal generators and the combiners. Besides, in one embodiment, the combiner 20, 40 is optically transparent to the ambient (environmental) lights from the opposite side of the incident light signals so that the viewer can observe the real-time image at the same time. The degree of transparency can vary widely depending on the application. For AR/MR application, the transparency is preferred to be more than 50%, such as about 75% in one embodiment.

The combiner 20, 40 may be made of glasses or plastic materials like lens, coated with certain materials such as metals to make it partially transparent and partially reflective. One advantage of using a reflective combiner instead of a wave guide in the prior art for directing light signals to the viewer's eyes is to eliminate the problem of undesirable diffraction effects, such as multiple shadows, color displacement . . . etc.

The foregoing description of embodiments is provided to enable any person skilled in the art to make and use the subject matter. Various modifications to these embodiments will be readily apparent to those skilled in the art, and the novel principles and subject matter disclosed herein may be applied to other embodiments without the use of the innovative faculty. The claimed subject matter set forth in the claims is not intended to be limited to the embodiments shown herein but is to be accorded the widest scope consistent with the principles and novel features disclosed herein. It is contemplated that additional embodiments are within the spirit and true scope of the disclosed subject matter. Thus, it is intended that the present invention covers modifications and variations that come within the scope of the appended claims and their equivalents.

What is claimed is:

1. A system for improving binocular vision, comprising:
    a virtual image module configured to display a first virtual object by projecting multiple normal light signals to a viewer's first eye and corresponding multiple adjusted light signals to the viewer's second eye;
    wherein the virtual image module displays the first virtual object within a field of view of the viewer's first eye and a field of view of the viewer's second eye, the first virtual object moving from a first targeted location and a first targeted depth to a second targeted location and a second targeted depth; and wherein the first targeted depth is related to a first convergence angle between the first normal light signal and a corresponding first adjusted light signal, the second targeted depth is related to a second convergence angle between the second normal light signal and a corresponding second adjusted light signal, and the first targeted depth is different from the second targeted depth, wherein the adjusted light signal projected to the viewer's second eye changes more in light direction than the normal light signal projected to the viewer's first eye, when the virtual image module displays the first virtual object moving from a first targeted location and a first targeted depth to a second targeted location and a second targeted depth.

2. The system of claim 1, wherein the normal light signal projected to the viewer's first eye does not change the light direction, when the virtual image module displays the first virtual object moving from a first targeted location and a first targeted depth to a second targeted location and a second targeted depth.

3. The system of claim 1, wherein the virtual image module displays the first virtual object moving from the second targeted location and the second targeted depth to a third targeted location and a third targeted depth while the adjusted light signal projected to the viewer's second eye changes more in light direction than the normal light signal projected to the viewer's first eye;

wherein the third targeted depth is related to the third angle between a third normal light signal and a corresponding third adjusted light signal, and the third targeted depth is different from the second targeted depth.

4. The system of claim 1, wherein, the virtual image module adjusts a spatial frequency of the first virtual object so that the first virtual object has a lower spatial frequency when the first virtual object is displayed at a greater depth, when the first virtual object is moved from the first targeted depth to the second targeted depth.

5. The system of claim 1, further comprising an eye tracking module configured to provide eye information of the viewer, wherein the virtual image module configured to display the first virtual object by projecting multiple normal light signals to the viewer's first eye to form a normal image and corresponding multiple adjusted light signals to the viewer's second eye to form an adjusted image based on the viewer's eye information from the eye tracking module, the eye tracking module provides eye information of the viewer's both eyes, including at least one of pupil location, pupil size, gaze angle, vergence angle, fixation location, and fixation depth.

6. The system of claim 5, wherein the virtual image module displays the first virtual object based on locations of the viewer's pupils provided by the eye tracking module so that the first eye perceives the normal image and the second eye perceives the adjusted image concurrently.

7. The system of claim 5, wherein the adjusted image has higher contrast or lower spatial frequency than a corresponding normal image.

8. The system of claim 5, wherein the virtual image module selects a contrast and a spatial frequency for the adjusted image based on a visual evoked potential (VEP) of the viewer's eye.

9. The system of claim 5, wherein the adjusted image is different but sufficiently related to the normal image for binocular fusion.

10. The system of claim 5,
wherein the eye tracking module provide fixation locations and fixation depths of the viewer's eyes to the virtual image module;
wherein the first targeted location and the first targeted depth are respectively a first fixation location and a first fixation depth, and the second targeted location and the second targeted depth are respectively a second fixation location and a second fixation depth.

11. The system of claim 10, wherein the virtual image module displays a second virtual object at a predetermined location and a predetermined depth, and the second virtual object is altered to interact with the first virtual object when the first virtual object moves within a predetermined spatial range of the second virtual object for a predetermined period of time.

12. The system of claim 11, wherein the second virtual object is altered to interact with the first virtual object when the first virtual object is moved to superimpose on the second virtual object.

13. The system of claim 10, further comprising:
a real object measuring module configured to measure a location and a depth of a real object.

14. The system of claim 13, wherein a feedback is given to the viewer when the first virtual object is moved within a predetermined spatial range of the real object.

15. The system of claim 10, wherein the virtual image module is calibrated for the viewer so that the viewer perceives the first virtual object displayed at a fixation location and a fixation depth.

16. The system of claim 5, wherein the virtual image module further comprises
a normal light signal generator generating multiple normal light signals for the normal image of the first virtual object;
a normal combiner redirecting the multiple normal light signals towards a retina of the viewer's first eye;
an adjusted light signal generator generating multiple adjusted light signals for the adjusted image of the first virtual object; and
an adjusted combiner redirecting the multiple adjusted light signals towards a retina of the viewer's second eye.

17. The system of claim 1, further comprising:
a VEP measuring module to measure a visual evoked potential (VEP) of the viewer's eye; and
wherein the virtual image module displays the first virtual object based on the VEP from the VEP measuring module.

18. The system of claim 17, wherein the virtual image module moves the first virtual object based on the viewer's VEP or locations of the viewer's pupils.

19. The system of claim 1, further comprising:
a feedback module configured to provide a feedback to the viewer when a predetermined condition is satisfied.

* * * * *